(12) United States Patent
Feldman et al.

(10) Patent No.: US 6,494,832 B1
(45) Date of Patent: Dec. 17, 2002

(54) MULTIFREQUENCY CONDUCTANCE CATHETER-BASED SYSTEM AND METHOD TO DETERMINE LV FUNCTION IN A PATIENT

(75) Inventors: Marc D. Feldman, San Antonio; Jonathan W. Valvano; John A. Pearce, both of Austin, all of TX (US)

(73) Assignee: Conductance Technologies, Inc., San Antonio, TX (US)

( * ) Notice: Subject to any disclaimer, the term of this patent is extended or adjusted under 35 U.S.C. 154(b) by 0 days.

(21) Appl. No.: 09/649,727

(22) Filed: Aug. 28, 2000

Related U.S. Application Data

(63) Continuation-in-part of application No. 09/265,092, filed on Mar. 9, 1999, now Pat. No. 6,112,115.

(51) Int. Cl.[7] .............................................. A61B 5/00
(52) U.S. Cl. ...................................................... 600/301
(58) Field of Search ................................ 600/513, 547, 600/300, 301, 483, 485

(56) References Cited

PUBLICATIONS

Timothy J. Gawne, Kristen S. Gray, Robert E. Goldstein, "Estimating left ventricular offset volume using dual–frequency conductance catheters", *J. Appl. Physiology*, vol. 63, pp. 872–876, 1987.

Millar MCS–100 System sales brochure, 1997.

*Primary Examiner*—Scott M. Getzow
(74) *Attorney, Agent, or Firm*—Ansel M. Schwartz

(57) ABSTRACT

An apparatus and method for determining cardiac performance in a patient. The apparatus includes a multifrequency conductance catheter for measuring instantaneous volume of a heart chamber with multifrequencies. The apparatus includes a mechanism for measuring instantaneous pressure of the heart chamber. The apparatus includes a mechanism for separating the multifrequencies. The apparatus includes a mechanism for signal processing the instantaneous volume and the pressure of the heart chamber to identify mechanical strength of the chamber and for automatically producing a plurality of desired waveforms at desired frequencies for the conductance catheter. The processing mechanism is connected to the pressure measuring mechanism, the separating mechanism and the volume measuring mechanism.

27 Claims, 8 Drawing Sheets

MULTIFREQUENCY CONDUCTANCE CATHETER-BASED SYSTEM AND METHOD TO DETERMINE LV FUNCTION IN A PATIENT

This application is a continuation-in-part of application Ser. No. 09/265,092 filed on Mar. 9, 1999 now U.S. Pat. No. 6,112,115.

FIELD OF THE INVENTION

The present invention is related to determining cardiac performance in a patient. More specifically, the present invention is related to determining cardiac performance in a patient with a conductance catheter which can be excited with multiple frequencies.

BACKGROUND OF THE INVENTION

Although there are other methods to measure ventricular volumes such as MRI and nuclear technologies, they cannot do so instantaneously. Echocardiography can generate an estimate of instantaneous volume using the modified Simpsons rule or "stack of discs". Because it utilizes a single tomographic plane to estimate three dimensional volumes, it has limitations when applied to patients with regional wall motion abnormalities. Therefore, only improvements in conductance technology offer the ability to make these precise mechanical measurements.

One conductance apparatus commercially available is the Cardiac Function Analyzer made by CardioDynamics in the Netherlands. This apparatus includes the Leycom Sigma 5, a device which is used to measure instantaneous volume from a conductance catheter. The Leycom Sigma 5 has been able to generate adequate volume data in ventricular chambers of large animals which are smaller than 150 ml. However, in patients with congestive heart failure, hearts may range from 180 to 500 ml. It has been previously shown (Reprint 1) that the Sigma 5 cannot generate a homogeneous electric field for volumes seen in human heart failure. Furthermore, there is no built in mechanism for the Sigma 5 to correct for current leakage into the surrounding conductive structures such as myocardium. As a result, it significantly underestimates the stroke volume (volume of blood pumped by the failing heart) and overestimates end-systolic and end-diastolic volumes. In reprints 2–5, there was an average 2-fold underestimation of the stroke volume. U.S. Patent to Carlson teaches that parallel conductance (current leakage outside the blood volume i.e., heart muscle) will be constant at different frequencies, so that this term can be excluded (see column 4, item (6)). Gwane et al. J Appl Physiology vol 63, pg 872–876, 1987 teaches that parallel conductance does vary with frequency, while By stroke volume is constant. The present invention is based on the discovery that since muscle resistivity does vary with frequency and blood does not, the resistivity ratio of blood and muscle will vary with frequency. Hence, both the field density within the left ventricle and the current leakage to the surrounding heart muscle both vary with frequency. The end result is both stroke volume and parallel conductance varying with frequency, which is in contrast to both the Carlson patent and Gwane paper. The apparatus uses a digitally controlled signal synthesizer to drive any conductance catheter. This results in more consistent control over waveform shape, amplitude, and frequency than known before. The use of the digital synthesizer also allows the user to select any type of waveform over a broad range of frequencies to apply to a conductance catheter. The digital signal synthesizer is a Signametrics Complex DDS Generator. The device can couple with commercially available conductance catheters made by numerous vendors. One includes Millar Instruments in Houston, Tex. They market conductance catheters with an incorporated Mikrotip pressure transducer for small animals including transgenic mice (SPR 719) and humans (SPC 550, 560, and 570).

The ability to delete single genes from small animals (mice and rats) to generate transgenic animals is now possible. This allows the study of the effect of a single gene deletion on the development on congestive heart failure (weak heart muscle) and hypertrophy (thickened heart muscle). Investigators are currently utilizing left ventricular pressure or its first derivative (dP/dt); or dimension and fractional shortening (derived by echocardiography). The problem with these isolated pressure and dimension measurements is that they are altered just by the heart size changes which accompany congestive heart failure and hypertrophy. Conductance catheter pressure-volume measurements miniaturized for the transgenic mouse allows the physiologic endpoint of how weak the heart muscle has become to be accurately determined. See "Cardiac physiology in transgenic mice" by James et al., and another paper demonstrating the technique of conductance PV loops in the mouse (Georgakopoulos et al. Am J Physiology 1998), both of which are incorporated by reference herein.

Conductance measurement offers a method to generate an instantaneous left ventricular volume signal in the mouse (Georgakopoulos D, Mitzner W A, Chen C H, Byrne B J, Millar H D, Hare J M, Kass D A. In vivo murine left ventricular pressure-volume relations by miniaturized conductance micromanometry. Am J Physiol 274 (Heart Circ Physiol 43): H1416–H1422, 1998, incorporated by reference herein). It uses an electric field generated from electrodes at the apex and immediately above the left ventricle to sense the instantaneous conductance change as the left ventricle fills and ejects blood. A signal proportional to the left ventricular blood volume is required for use in physiologic studies. Unfortunately, the presently available instantaneous conductance output is a combination of blood and left ventricular muscle (Boltwood C M, Appleyard R F, Glantz S A. Left ventricular volume measurement by conductance catheter in intact dogs: parallel conductance volume depends on left ventricular size. Circulation 80: 1360–1377, 1989; Burkhoff D, Van Der Velde E, Kass D, Baan J, Maughan W L, Sagawa K. Accuracy of volume measurement by conductance catheter in isolated, ejecting canine hearts. Circulation 72: 440–447, 1985; Cabreriza S E, Dean D A, Jia C X, Dickstein M L, Spotnitz H M. Electrical isolation of the heart: stabilizing parallel conductance of left ventricular volume measurement. ASAIO Journal 43: M 509-M 514, 1997; Lankford E B, Kass D A, Maughan W L, Shoukas A A. Does parallel conductance vary during a cardiac cycle? Am J Physiol 258 (Heart Circ Physiol 27): H1933–H1942, 1990; Szwarc R S, Mickleborough L L, Mizuno S I, Wilson G J, Liu P, Mohamed S. Conductance catheter measurements of left ventricular volume in the intact dog: parallel conductance is independent of left ventricular size. Cardiovas Res 28: 252–258, 1994, all of which are incorporated by reference herein). By developing a conductance system that operates at several simultaneous frequencies, identification and possibly correction for the myocardial contribution to the instantaneous volume signal can be had.

This is based on the assumption that patient myocardial conductivity will vary with frequency, while patient blood conductivity will not. Prior work has shown that blood has constant electrical resistivity over a wide range of frequencies (2 to 100 kHz, 22). In contrast, the resistivity of myocardium is known to change with frequency; specifically, the resistivity of myocardium is lower at increased excitation frequency (Epstein B R, Foster K R. Anisotropy in the dielectric properties of skeletal muscle. Med Biol Eng Comput 21: 51–55, 1983; Schwan H P, Kay C F. Specific resistance of body tissues. Circ Res IV: 664–670, 1956; Steendijk P, Mur G, Van Der Velde E, Baan J. The four-electrode resistivity technique in anisotropic media: theoretical analysis and application on myocardial tissue in vivo. IEEE Trans Bio Med Eng 40: 1138–1148, 1993; Steendijk P, Mur G, Van Der Velde E, Baan J. Dependence of anisotropic myocardium electrical resistivity on cardiac phase and excitation frequency. Basic Res Cardiol 89: 411–426, 1994; Zheng E, Shao S, Webster J G. Impedance of skeletal muscle from 1 Hz to 1 MHz. IEEE Trans Biomed Eng 31: 477–483, 1984, all of which are incorporated by reference herein). See FIG. 1. At lower frequencies, there is a maximal gradient between the resistivity of blood and myocardium such that the electric field generated will be primarily confined to the left ventricular cavity and to a lesser degree in the myocardium. At higher frequencies, there will be a minimal gradient between the resistivity of blood and myocardium and the electric field generated will not be confined to the left ventricular cavity but extend into the myocardium. Accordingly, the higher the excitation frequency, the greater the apparent end-diastolic and end-systolic conductance detected by the miniaturized conductance catheter. In addition, if this construct is correct there should be a slight reduction in the difference between end-diastolic and end-systolic conductance at higher frequencies since the relative proportion of the signal changing from systole to diastole is smaller.

This approach could have an important advantage over the traditional conductance method for determining measures of ventricular function such as end-systolic elastance. Since elastance is generated during beat-by-beat changes in loading conditions, a method to determine and correct for instantaneous parallel conductance is critical and does not exist. The use of multiple simultaneous frequencies has the potential to solve this problem. The application of this approach would be in transgenic mice. There is need to relate specific gene products to phenotype. Unfortunately, the ability to rigorously assess the cardiovascular phenotype in very small animals has lagged (Christensen G, Wang Y, Chien K. Physiologic assessment of complex cardiac phenotypes in genetically engineered mice. Am J Physiol 272 (Heart Circ Physiol 41): H 2513–H 2524, 1997, James J F, Hewett T E, Robbins J. Cardiac physiology in transgenic mice. Circ Res 82: 407–415, 1998, both of which are incorporated by reference herein). Such analysis has been available in larger animals by measurement of simultaneous left ventricular pressure and volume to examine cardiac performance in the pressure-volume plane (Baan J, Van Der Velde E T, De Bruin H G, Smeenk G J, Van Dijk A D, Temmerman D, Senden J, Buis B. Continuous measurement of left ventricular volume in animals and humans by conductance catheter. Circulation 70: 812–823, 1984; Kass D A, Yamazaki T, Burkhoff D, Maughan W L, Sagawa K. Determination of left ventricular end-systolic pressure-volume relationships by the conductance (volume) catheter technique. Circulation 73: 586–595, 1986, both of which are incorporated by reference herein). The application of this approach to mice has been difficult due to the small size of the mouse heart and the rapid heart rate. Creating technology to generate an accurate instantaneous volume signal in the transgenic mouse to generate pressure-volume relationships during occlusion of the inferior vena cava is a goal of this study.

By combining experimental data with an analytical approach consisting of a series of equations it was possible to extract an accurate estimate of left ventricular blood and myocardial components.

SUMMARY OF THE INVENTION

The present invention pertains to an apparatus for determining cardiac performance in a patient. The apparatus comprises a multifrequency conductance catheter for measuring instantaneous volume of a heart chamber with multifrequencies. The apparatus comprises a mechanism for measuring instantaneous pressure of the heart chamber. The apparatus comprises a mechanism for separating the multifrequencies. The apparatus comprises a mechanism for signal processing the instantaneous volume and the pressure of the heart chamber to identify mechanical strength of the chamber and for automatically producing a plurality of desired waveforms at desired frequencies for the conductance catheter. The processing mechanism is connected to the pressure measuring mechanism, the separating mechanism and the volume measuring mechanism.

At The present invention pertains to a method for determining cardiac performance in a patient. The method comprises the steps of inserting a conductance catheter into an in vivo heart. Next there is the step of sending simultaneously a combined signal consisting of at least two frequencies from a signal source into an amplifier. Then there is the step of applying a current to outer electrodes of the conductance catheter. Next there is the step of measuring an instantaneous voltage signal from the heart with intermediate electrodes of the conductance catheter. Then there is the step of extracting from the intermediate electrodes the combined signal potential from the combined signal. Next there is the step of separating the frequencies from the combined signal potential. Then there is the step of determining the separate conductance associated with each frequency. Next there is the step of identifying pressure volume loops regarding the heart of the patient.

BRIEF DESCRIPTION OF THE DRAWINGS

In the accompanying drawings, the preferred embodiment of the invention and preferred methods of practicing the invention are illustrated in which:

FIG. 5a is the conductance derived left ventricular pressure-conductance relationships during hypertonic saline wash-in used to calculate end-systolic and end-diastolic conductance on a beat-by-beat basis shown in FIG. 5b. FIG. 5b demonstrates the calculation of parallel conductance using equations (3) and (4) in the Methods. Parallel conductance was 554.24 $\mu$S.

DETAILED DESCRIPTION

Figure 1:
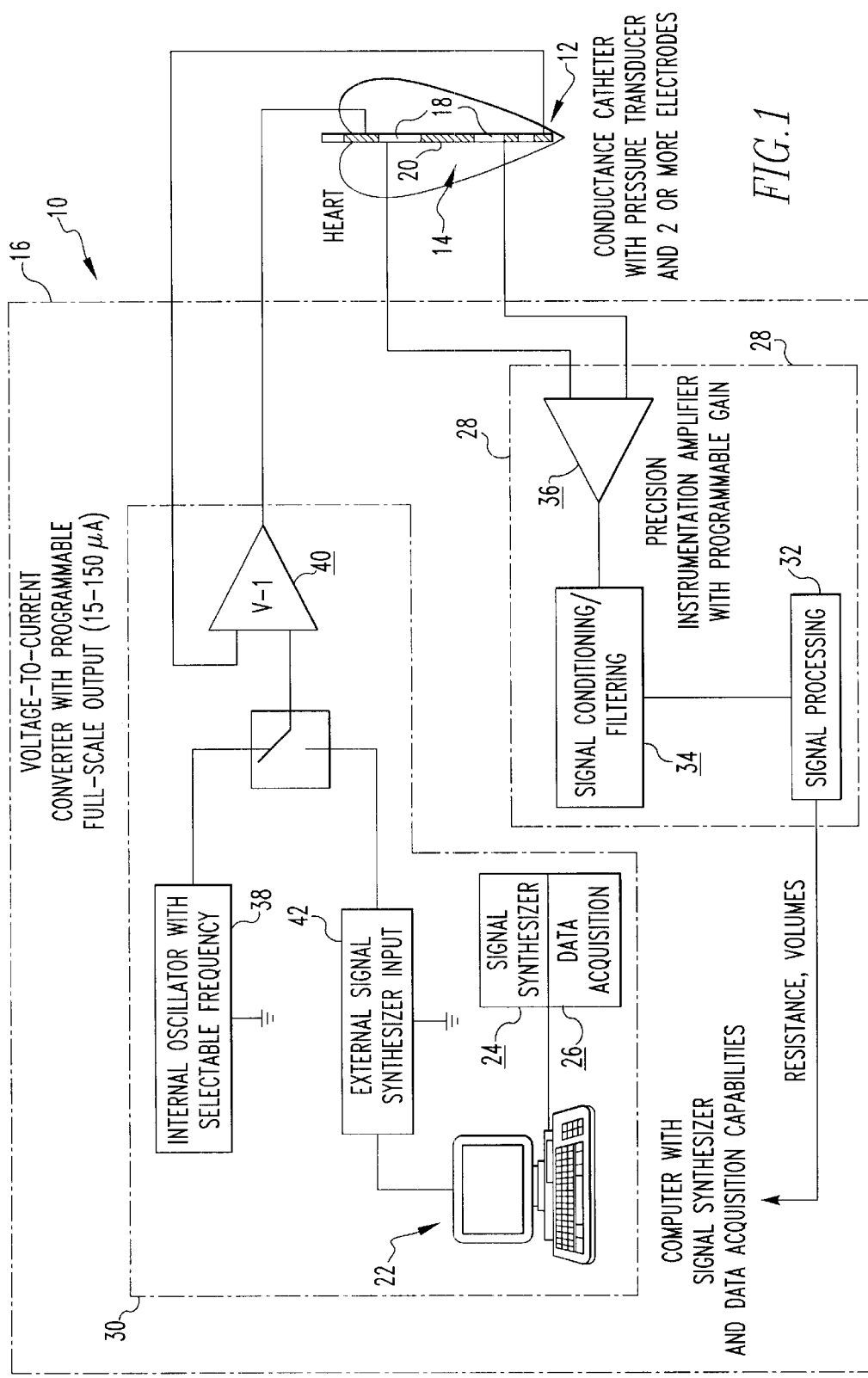
FIG. 1 is a schematic representation of an apparatus of the present invention.

Referring now to the drawings wherein like reference numerals refer to similar or identical parts throughout the several views, and more specifically to FIG. 1 thereof, there is shown an apparatus 10 for determining cardiac performance in a patient. The apparatus 10 comprises a multifrequency conductance catheter 12 for measuring instantaneous volume of a heart chamber. The apparatus 10 comprises a mechanism 14 for measuring instantaneous pressure of the heart chamber. The apparatus 10 comprises a signal processing mechanism 16 for processing the instantaneous volume and the pressure of the heart chamber to identify mechanical strength of the chamber and for automatically producing a plurality of desired waveforms at desired frequencies for the conductance catheter 12. The processing mechanism 16 is connected to the pressure measuring mechanism 14 and the catheter 12.

Preferably, the conductance catheter 12 includes a plurality of electrodes 18 to measure at least one segmental volume of the heart chamber. The conductance catheter 12 preferably includes at least one pressure sensor 20 to measure ventricular pressure in the chamber. Preferably, the electrodes 18 measure the EKG.

The signal processing mechanism 16 preferably combines the instantaneous volume and pressure with a first derivative of pressure to identify the mechanical strength of the chamber.

The signal processing mechanism 16 preferably includes a computer 22 with a signal synthesizer 24 and a data acquisition mechanism 26 connected to the catheter 12. Preferably, the signal processing mechanism 16 includes a mechanism 28 for converting conductance into a volume. The converting mechanism 28 is connected to the catheter 12 and the computer 22. Preferably, the converting mechanism 28 includes signal processing circuitry 32 for converting measured conductance to a volume. The signal processing circuitry 32 is connected to the catheter 12 and the computer 22.

The converting mechanism 28 preferably includes a signal conditioning/filter mechanism 34 for reducing noise level of measured conductance. The signal conditioning/filter mechanism 34 is connected to the signal processing circuitry 32 and the computer 22. Preferably, the converting mechanism 28 includes a precision amplifier 36 which amplifies a potential differential across the electrodes 18, said pressure amplifier 36 connected to the catheter 12 and the signal conditioning/filter mechanism 34.

The signal processing mechanism 16 preferably includes a mechanism 30 for producing a drive signal to drive the conductance catheter 12. The producing mechanism is connected to the catheter 12 and the computer 22.

The drive mechanism 30 preferably includes an internal oscillator 38 which generates an amplitude excitation voltage at least at two different frequencies. The internal oscillator 38 is connected to the computer 22 and the catheter 12. Preferably, the drive mechanism 30 includes a voltage-to-current converter 40 which converts excitation voltage to a current. The voltage-to-current converter 40 is connected to the internal oscillator 38 and the catheter 12. Preferably, the drive mechanism 30 includes a signal synthesizer 24 of the computer 22 which controls the external input signal synthesizer 42, which controls the voltage-to-current converter 40.

The present invention pertains to a method for determining cardiac performance in a patient. The method comprises the steps of applying automatically multifrequencies to a conductance catheter 12.

Then there is the step of measuring the instantaneous volume of a heart chamber of the patient. Next there is the step of measuring the instantaneous pressure of the heart chamber. Then there is the step of identifying mechanical strength of the chamber from the instantaneous volume and pressure. Preferably, the measuring the volume step includes the step of measuring the volume with a conductance catheter 12.

In the operation of the invention, the purpose of the multifrequency conductance apparatus 10 is to evaluate ventricular mechanics by means of the pressure-volume relationship. A major component of the apparatus 10 is a device which can measure instantaneous volume from a heart chamber using the conductance catheter 12. The instantaneous volume signal can then be coupled with pressure, and the first derivative of pressure to provide gold standard measures of the mechanical strength of the ventricle. These measures are made by manipulating the preload to the ventricular chamber as instantaneous pressure and volume are plotted against one-another.

The conductance apparatus 10 which can be excited with multiple frequencies is capable of correcting for errors resulting from frequency dependent conductance of surrounding structures, in short, correcting for the effect of parallel conductance. This may allow a change in conductance catheter 12 design where the more proximal driving electrode is moved away from the ventricle, which may improve the homogeneity of electric field within the ventricular chamber. Without proper correction, such an advantage in field distribution is negated by more parallel conductance. The multifrequency conductance apparatus 10 makes such important advances in conductance catheter 12 design feasible.

The apparatus 10 uses a digitally controlled signal synthesizer 24 to drive the conductance catheter 12. This results in consistent and more accurately controlled waveform shape, amplitude and frequency. The use of a digital synthesizer also allows the user to select any type of waveform over a broad range of frequencies to apply to the conductance catheter 12. These two features are unique to this apparatus 10 and not available in the Leycom Sigma 5, or products of other companies including BioMetrics, Inc., Las Vegas, Nev.

The multifrequency conductance apparatus 10 allows the user to set the operating current of the apparatus 10, within a physiologically safe range. The ability of the apparatus 10 to operate at currents higher than the 30 $\mu$A RMS current available with the Leycom Sigma 5 improves the signal to noise ratio of the measured signal. This feature makes the proposed apparatus 10 useful in situations in which the signal to noise ratio may be poor. For example, this apparatus 10 may be used for conductance studies in mouse hearts which have undergone gene manipulation ("knock-out" mice). Pressure-volume relationships are critical in quantitating the physiologic effect of genetic manipulation of a mouse heart. However, the dimensions of the mouse heart require small electrode spacing, producing a poor signal to noise ratio of the measured volume signal. The ability to increase the applied current improves the signal to noise ratio and improves the quality of the measured volume signal in mice. These same results and applications can be used in other animals and in humans. The only change is that an appropriate sized catheter 12 be used for the given patient.

The apparatus 10 consists of multiple components with features outlined in FIG. 1.

(a) The apparatus 10 includes a voltage-controlled constant current source for any configuration of conductance catheter 12 with a means for applying a constant alternating current (AC) using a digital signal synthesizer 24. The digital signal synthesizer 24 is used to select any type of waveform over a broad range of frequencies.

Figure 2:
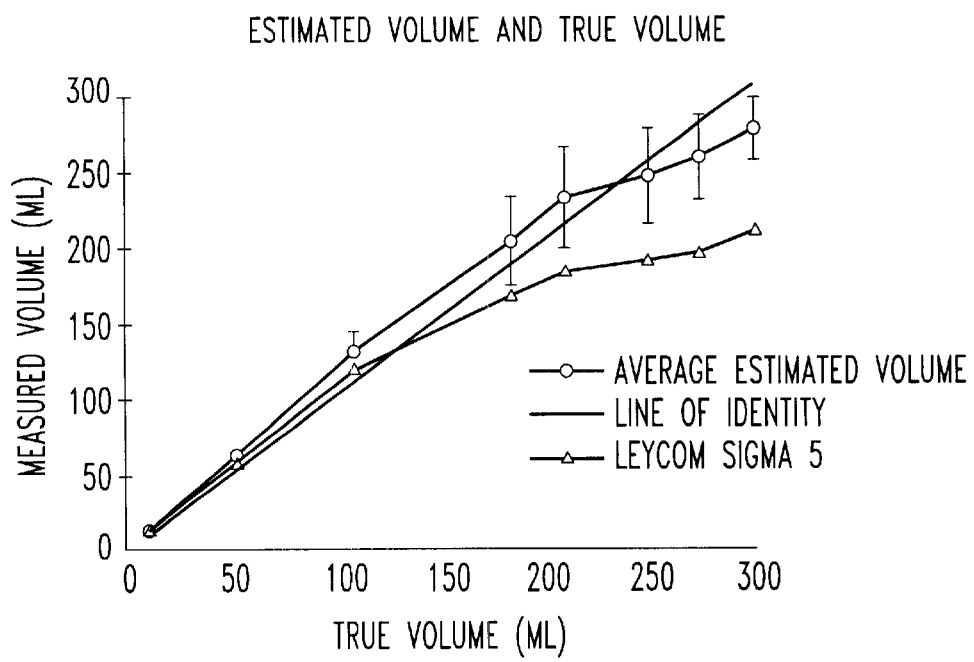
FIG. 2 is a graph of the true volume vs. measured volume.

(b) The apparatus 10 contains analog circuitry which is used for signal conditioning and can be used to measure the conductance signal from any configuration of conductance catheter 12. The conductance signal is converted to volume based on the equation:

$$V = \frac{L^2 * G}{\delta}$$

where V=volume of the heart muscle chamber, L=the distance between the measuring electrodes 18 on the conductance catheter 12, $\delta$=the conductivity of blood, and G=conductance. Data from the apparatus 10 is shown in FIG. 2. The apparatus 10 being disclosed shows improved performance over the existing Leycom Sigma 5.

In FIG. 2, true volume is displayed on the x-axis. Measured conductance volumes for the multifrequency conductance apparatus 10 being disclosed (open circles) are displayed as Mean±SE for three runs. The measured conductance volumes for the competing Leycom Sigma 5 are also shown (open triangles). The solid line is the line of identity. In larger volumes seen clinically, the device being disclosed estimates true volume more closely than the Leycom Sigma 5 did.

Figure 3:
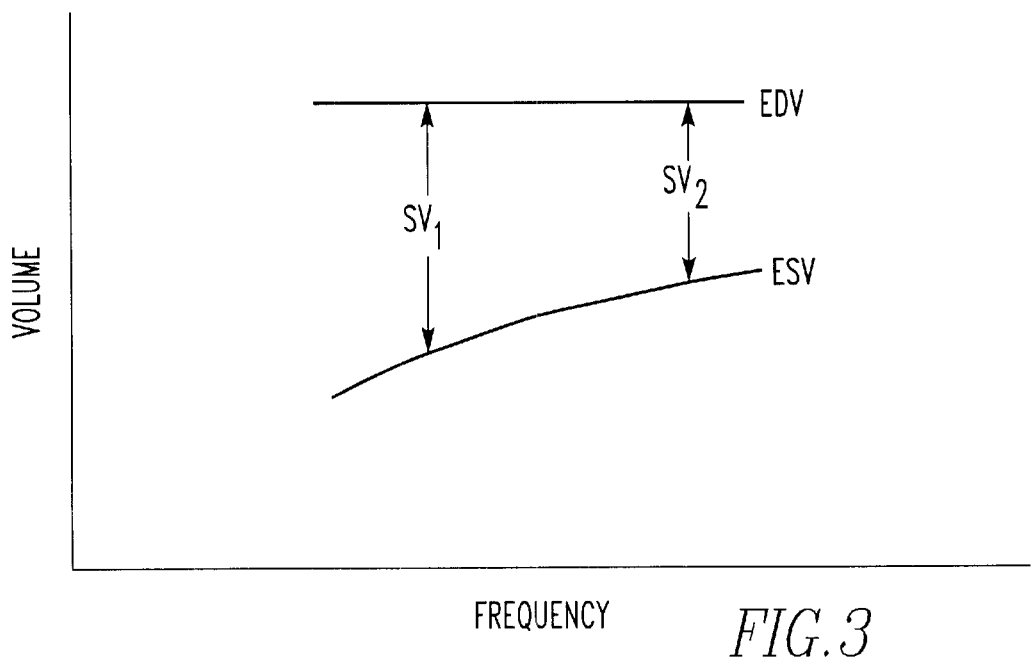
FIG. 3 is a graph of volume vs. frequency.
Figure 4A:
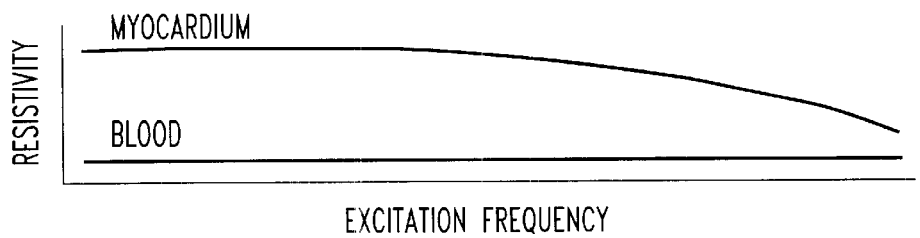
FIG. 4 is a depiction that the higher the excitation frequency, the greater the end-diastolic and end-systolic volume detected by the miniaturized conductance catheter. In addition, there should be a slight reduction in stroke volume at higher frequencies since the field density contained within the left ventricular blood is reduced.
Figure 4B:
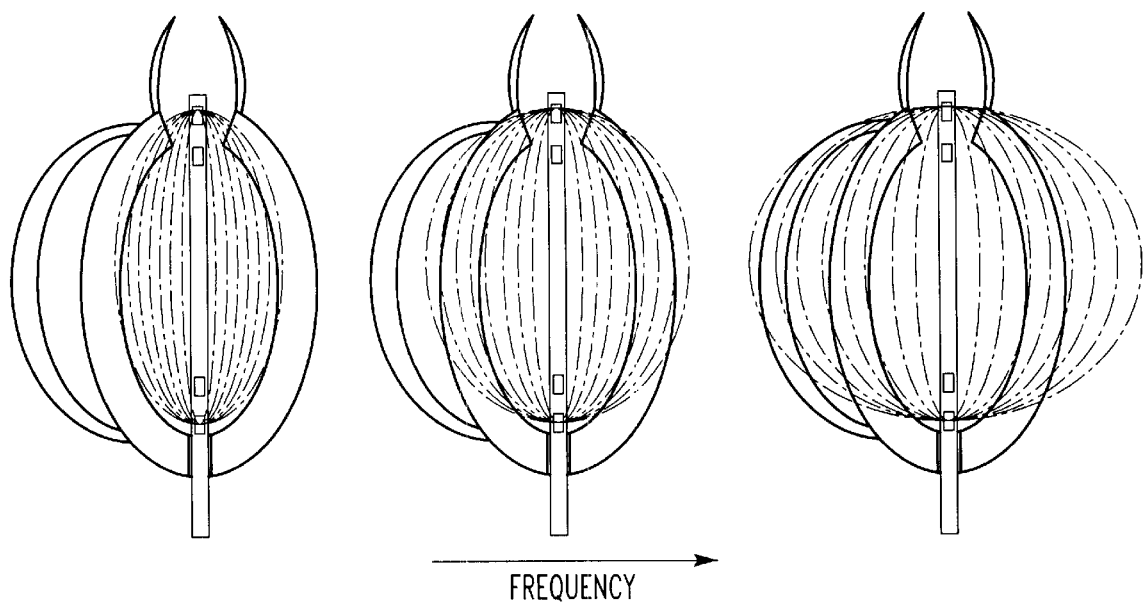

(c) The apparatus 10 provides a method for estimating the true stroke volume by measuring volume at multiple frequencies. End-contractions (end-systolic) and end-relaxation (end-diastolic) volumes are plotted versus frequency to obtain a linear relationship as illustrated in FIG. 3. The difference between these volumes or the amount of blood ejected by the heart to the body is termed stroke volume (SV). The end-systolic and end-diastolic volumes generated by the multifrequency conductance apparatus 10 and the Leycom Sigma 5 are both artificially large due to parallel conductance. Since SV varies with frequency (i.e. $SV_1 > SV_2$), and ESV and EDV also vary with frequency, parallel conductance can be derived, and true stroke volume, EDV and ESV derived. Once an estimate of the true stroke volume, EDV, and ESV is obtained, all gold standard hemodynamic parameters in conjunction with occlusion of the inferior vena cava can be accurately derived. End-systolic elastance of one patient can be compared to another, which has not been previously possible.

The Leycom Sigma 5 and BioMetrics cannot be used this way because they operate at a single fixed frequency. Since occlusion of the inferior vena cava to change blood pressure on a beat-by-beat basis is used to generate measures of heart muscle strength, current leakage into surrounding heart structures will be changing on a beat-by-beat basis, thus affecting the accuracy in measuring stroke volume, EDV and ESV. As a result, a feature made possible by the apparatus 10 is critical to be able to compare the results of one patient to the next.

(d) The apparatus 10 provides the means for not only acquiring volume but also other signals critical for calculating hemodynamic indices such as pressures in the heart, and the electrocardiogram. All these signals may be acquired and processed using an integrated signal processor.

(e) The apparatus 10 has the software capabilities to calculate gold standard hemodynamic indices to distinguish the strength of the heart (end-systolic pressure volume relationships, preload recruitable stroke work, end-diastolic volume—dP/dt relationship) from the load the heart works against (end-systolic pressure and volume, end-diastolic pressure and volume, effective arterial elastance). Additional indices calculated include stroke volume, stroke work, positive and negative dP/dt, cardiac output, ejection fraction, peak filling rate, peak ejection rate, isovolumic relaxation time constant and preload adjusted maximal power.

The pressure/conductance catheter 12 for mice, model SPR-716, consists of a pressure sensor 20 located near the tip of a 0.25 mm diameter polyimide catheter 12, with two platinum ring electrodes 18 distal to the sensor and two platinum electrodes 18 proximal. The outer two electrodes 18 are spaced 5.5 mm apart, center to center, and the inner pair 4.5 mm apart. This configuration allows for the placement of the catheter 12 within the heart of a 20 gram mouse, with the pressure sensor 20 in the center of the ventricle, the field generating electrodes 18 at opposite ends of the ventricular chamber, one at the apex and one at the aortic valve, and the segment sensing electrodes 18 almost at the same location, but slightly closer to each other, to measure the electrical field distribution within the chamber.

The pressure sensor 20, with a diameter of 0.5 mm, has two strain gauges mounted on a thin flexible diaphragm, insulated and isolated from external fluids by a thin silicone rubber coating. As the diaphragm deflects slightly under applied pressure, the he strain gauges change resistance linearly with applied pressure, the one gauge increasing in resistance and the other gauge decreasing. Three wires from the strain gauges, along with a reference air vent to atmosphere, are carried through the catheter 12 to the connector at the proximal end. Within the connector is a resistance network to complete a bridge circuit for the transducer and provide the appropriate standardization of output, temperature compensation and bridge balancing.

The platinum ring electrodes 18 are approximately 0.37 mm in diameter and 0.25 mm long. Each one has a wire attached leading to a separate electrical connector for the conductance control unit. In a typical operating configuration, a 30 $\mu$A signal can be applied to the outer pair of field excitation electrodes 18, with the inner pair of electrodes 18 connected to an amplifier for measuring the conductance of the ventricle within the beating heart. Changes in conductance are proportional to the volume of electrically conductive blood within the chamber; the conductance control unit is configured to give an on-line analog signal output proportional to the volume of blood in the beating ventricle.

Computer 22 with Signal Synthesizer and data acquisition capabilities—The conductance-volume measurement apparatus 10 utilize a voltage-to-current converter 40 to generate the excitation field. A computer-controlled external synthesizer provides the user full control on waveform and current amplitude, thus allowing different excitation schemes to be tested to improve measurement accuracy. The data acquisition apparatus 10 allows the user to digitize the resistance or volume signals for post processing and data analysis.

Internal Oscillator 38—generate a fixed amplitude excitation voltage at multiple frequencies.

Voltage-to-current converter 40—convert the excitation voltage to a calibrated constant current over wide range of load.

Conductance catheter 12—contains 2 or more electrodes 18, intracardiac electric field is set up by applying the constant current with the catheter 12, the same or additional electrodes 18 are used to measure conductance in the ventricular chamber from which volumes are calculated.

Pressure amplifier 36—amplify the signal from the solid state pressure sensor 20.

Signal conditioning/filtering—after amplification, the measured signal may be filtered using one of the pre-programmed settings to reduce the noise level.

Signal processing circuitry 32—the measured conductance are converted to volume using processing techniques such as envelope detector and synchronous detector. The unprocessed signals is also available to the user for advanced signal analysis.

Figure 10:
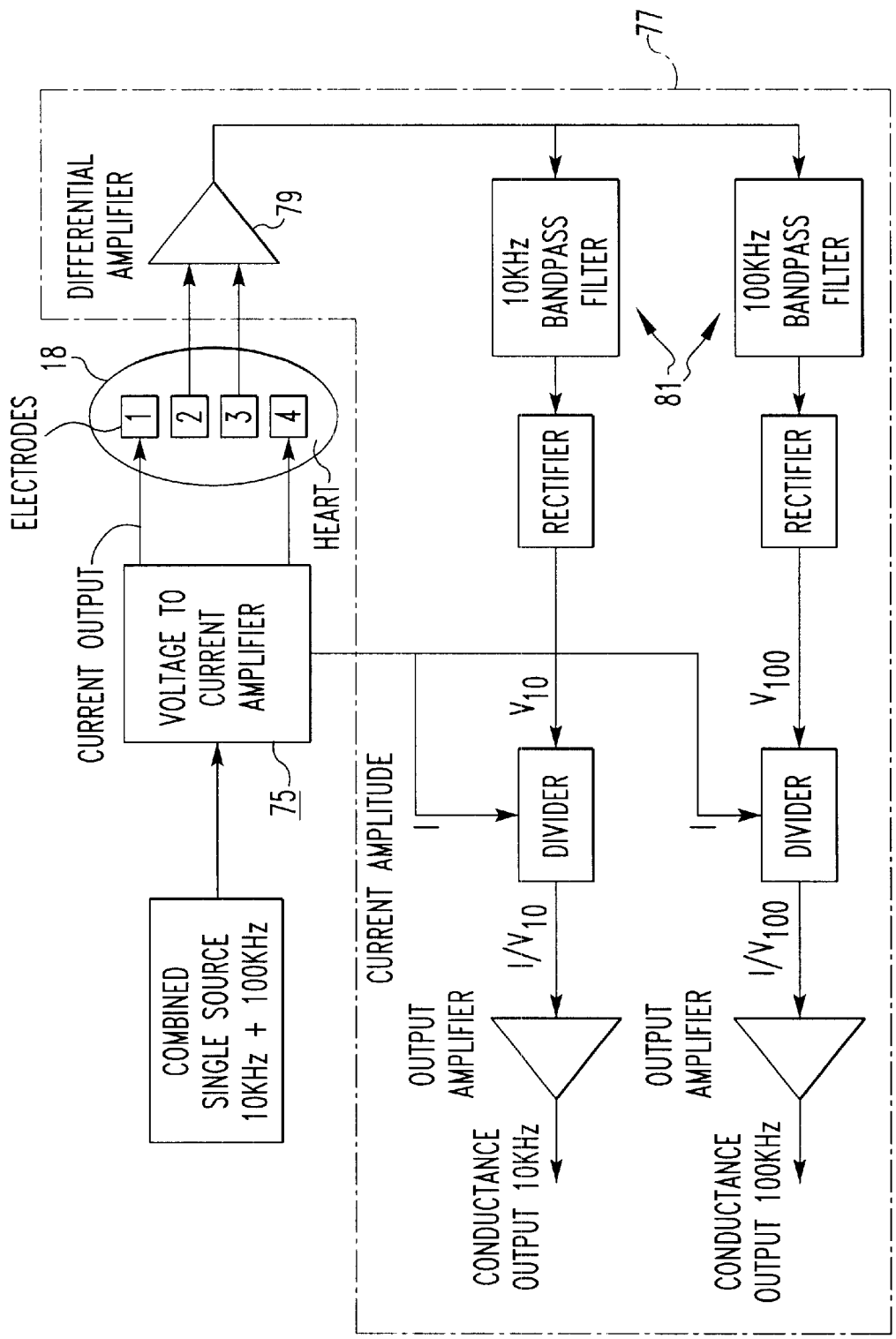
FIG. 10 is a schematic representation of the catheter, separating mechanism and the drive mechanism.
Figure 11:
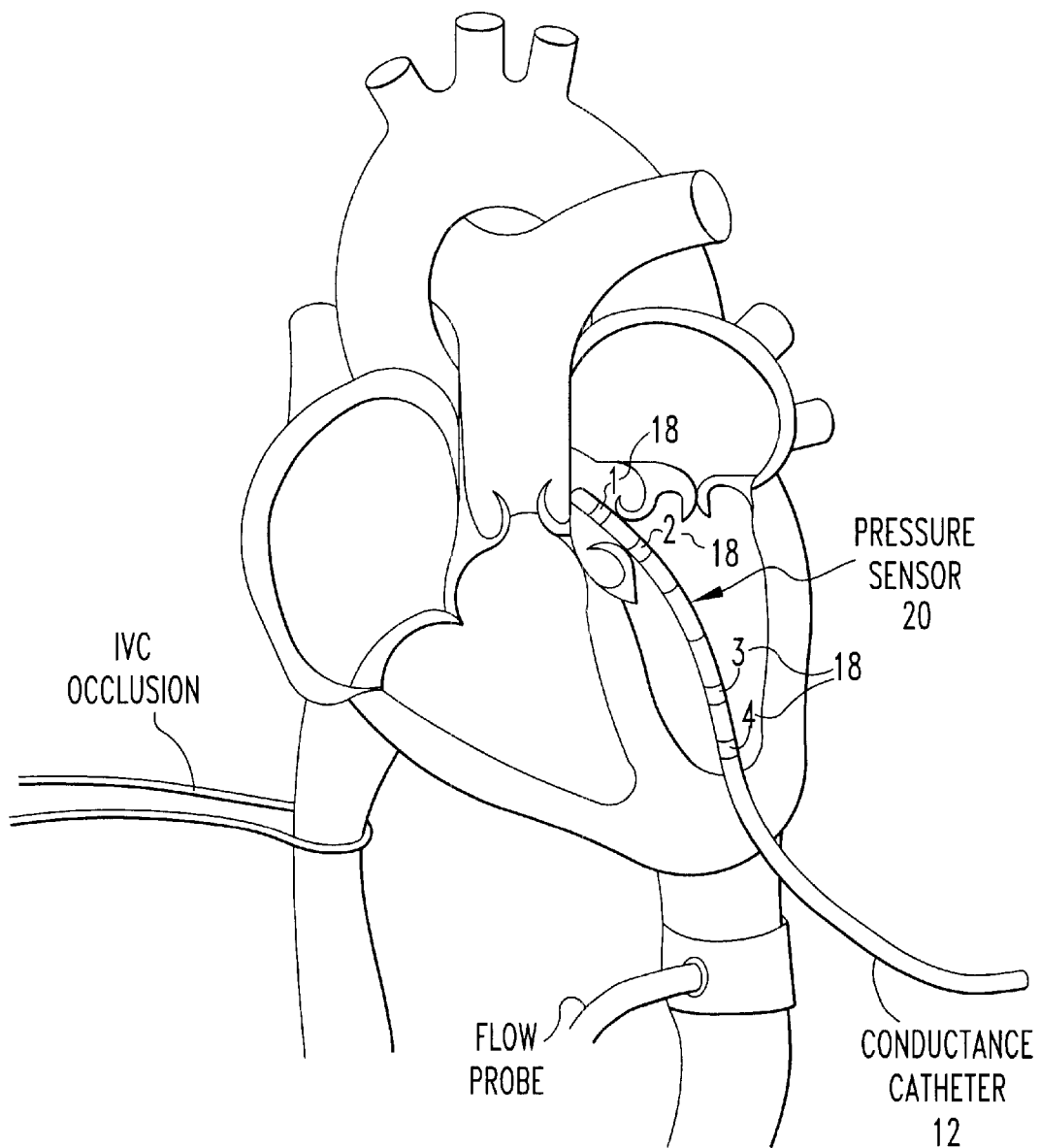
FIG. 11 is a schematic representation of the catheter in the heart.

The present invention pertains to an apparatus 10 for determining cardiac performance in a patient, as shown in FIGS. 1, 10 and 11. The apparatus 10 comprises a multi-frequency conductance catheter 12 for measuring instantaneous volume of a heart chamber with multifrequencies. The apparatus 10 comprises a mechanism for measuring instantaneous pressure of the heart chamber. The apparatus 10 comprises a mechanism 77 for separating the multifrequencies. The apparatus 10 comprises a mechanism for signal processing the instantaneous volume and the pressure of the heart chamber to identify mechanical strength of the chamber and for automatically producing a plurality of desired waveforms at desired frequencies for the conductance catheter 12. The processing mechanism is connected to the pressure measuring mechanism, the separating mechanism 77 and the volume measuring mechanism.

Preferably, the conductance catheter 12 includes a plurality of electrodes 18 to measure at least one segmental volume of the heart chamber. The plurality of electrodes 18 preferably includes intermediate electrodes 18 to measure an instantaneous voltage signal from the heart, and outer electrodes 18 to which a current is applied from the processing mechanism. Preferably, the conductance catheter 12 includes at least one pressure sensor 20 to measure ventricular pressure in the chamber. The pressure sensor 20 is preferably disposed between the intermediate electrodes 18 and the outer electrodes 18.

Preferably, the signal processing mechanism includes a computer with a signal synthesizer and a data acquisition mechanism connected to the catheter 12. The signal processing mechanism preferably includes a mechanism for converting conductance into a volume. The converting mechanism is connected to the catheter 12 and the computer. Preferably, the signal processing mechanism includes a mechanism for producing a drive signal to drive the conductance catheter 12. The producing mechanism is connected to the catheter 12 and the computer.

The converting mechanism preferably includes signal processing circuitry for converting measured conductance to a volume. The signal processing circuitry is connected to the catheter 12 and the computer. Preferably, the converting mechanism includes a signal conditioning/filter mechanism for reducing noise level of measured conductance. The signal conditioning/filter mechanism is connected to the signal processing circuitry and the computer.

The converting mechanism preferably includes a pressure amplifier which amplifies the signal from the solid state pressure sensor 20. The pressure amplifier is connected to the catheter 12 and the signal conditioning/filter mechanism. Preferably, the drive mechanism includes an internal oscillator which generates a combined signal source of an amplitude excitation voltage at least at two different frequencies. The internal oscillator is connected to the computer and the catheter 12. The drive mechanism preferably includes a voltage-to-current amplifier 75 which converts excitation voltage to a current. The voltage-to-current amplifier is connected to the internal oscillator and the catheter 12. Preferably, the drive mechanism includes an external input signal synthesizer mechanism for controlling the signal synthesizer of the computer to produce desired waveforms at desired frequencies. The external input signal synthesizer mechanism is connected to the computer.

The separating mechanism 77 preferably includes a differential amplifier 79 connected to the intermediate electrodes 18 which extracts a combined signal potential from the intermediate electrodes 18. Preferably, the separating mechanism 77 includes band-pass filters 81 connected to the differential amplifier which separates the frequencies from the combined signal potential.

The present invention pertains to a method for determining cardiac performance in a patient. The method comprises the steps of inserting a conductance catheter 12 into an in vivo heart. Next there is the step of sending simultaneously a combined signal consisting of at least two frequencies from a signal source into an amplifier. Then there is the step of applying a current to outer electrodes 18 of the conductance catheter 12. Next there is the step of measuring an instantaneous voltage signal from the heart with intermediate electrodes 18 of the conductance catheter 12. Then there is the step of extracting from the intermediate electrodes 18 the combined signal potential from the combined signal. Next there is the step of separating the frequencies from the combined signal potential. Then there is the step of determining the separate conductance associated with each frequency. Next there is the step of identifying pressure volume loops regarding the heart of the patient.

Preferably, the separating step includes the step of separating with active band-pass filters the frequencies from the combined signal potential. The extracting step preferably includes the step of extracting from the intermediate electrodes 18 with a common mode rejection differential amplifier the combined signal potential from the combined signal. Preferably, the sending step includes the step of sending simultaneously the combined signal consisting of at least two frequencies from a combined signal source into a voltage to current amplifier.

The applying step preferably includes the step of applying a constant current from the voltage to current amplifier to the outer electrodes 18 of the conductance catheter 12. Preferably, the identifying step includes the steps of determining instantaneous pressure of the heart from a pressure sensor 20 of the catheter 12, determining instantaneous volume of the heart from the conductances associated with each frequency and linking instantaneous pressure and instantaneous volume at the same time over time to generate pressure volume loops regarding the heart of the patient.

The multifrequency conductance-steps which occur-generalized.

1) The 4 electrode conductance catheter is inserted into an in vivo murine heart.
2) A combined signal source (synthesized 2-frequency cosine wave) consisting of 10 and 100 KHz is simultaneously sent into a voltage to current amplifier.
3) A constant current from the voltage to current amplifier is applied to electrodes 1 and 4 (outer electrodes).
4) Electrodes 2 and 3 (intermediate electrodes) are used to measure the instantaneous voltage signal from the beating heart.
5) The combined signal potential is extracted from electrodes 2 and 3 (intermediate electrodes) with a high common mode rejection differential amplifier.
6) The two frequencies are separated by analog active band-pass filters and the separate conductance determined after digital sampling and calibration in software.
7) The instantaneous pressure is determined from the pressure sensor.
8) The instantaneous volume is linked with the instantaneous pressure at the same time to generate pressure volume loops regarding the left ventricle of the patient.

In the operation of the preferred embodiment, a 1.4 French miniaturized pressure-volume catheter (SPR-719, Millar Instruments, Houston, Tex.) was used. The catheter has 4 platinum electrodes each 0.25 mm in length with inter-electrode spacing of 0.5 mm, 4.5 mm, and 0.5 mm between electrodes 1 and 2, 2 and 3, and 3 and 4, respectively. A constant excitation current (17 $\mu$A root mean square) was applied to the two outermost electrodes using a custom signal generator/processor and bridge amplifiers (MCS-100, Millar Instruments, Houston, Tex.) and the two intermediate electrodes were used to measure the instantaneous voltage signal. A high-fidelity pressure transducer (frequency response flat to 10 kHz) was mounted between electrodes 2 and 3 to measure ventricular pressure.

The theory behind the determination of volume using the conductance catheter in larger animals has been described in detail elsewhere (Mur G, Baan J. Computation of the input impedances of a catheter for cardiac volumetry. IEEE Trans Biomed Eng 31: 448–453, 1984, incorporated by reference herein). Briefly, the tetrapolar catheter generates an intraventricular electric field between the outer electrodes. The potential differences between the inner electrode pair are measured continuously and yields an instantaneous voltage output. The method of conversion of instantaneous voltage to instantaneous conductance for both single and dual frequency is given in the next 2 sections of the Methods. The time varying ventricular volume, V(t), is estimated from:

$$V_i(t) = (1/\alpha)\,(\rho L^2)\,(G_i(t) - G_{pi}) \qquad (1)$$

where $\alpha$ is the ratio of flow probe stroke volume to conductance stroke volume, $\rho$ is the blood resistivity, L is the distance between the sensing electrodes, $G_i(t)$ is the instantaneous conductance, and $G_{pi}$ is the instantaneous conductance of the surrounding structures particularly the left ventricular myocardium, or parallel conductance. Assuming the ratio of flow probe stroke volume to conductance stroke volume is 1, and no parallel conductance, then equation (1) simplifies to:

$$V_i(t) = (\rho L^2) G_i(t) \qquad (2)$$

Calculation of mouse blood volume from single frequency data. The signal processor provides an analog voltage output. A calibration procedure was developed to convert this voltage output into conductance ($\mu$S). Known resistors were used to calibrate the instrumentation. Since conductance is the inverse of resistance, these resistors are connected to the system as the input, and a corresponding voltage is derived. The relationship from the input conductance to the output voltage is then known. This relationship is added to the data acquisition software, to obtain instantaneous conductance from the beating mouse heart. That generates $G_i$, which is converted to volume using Baan's simplified equation (2), and not equation (1) since $G_{pi}$ was not known. Then subtraction of the steady state parallel conductance ($G_p$) derived by the hypertonic saline method (which will be described below) from the raw volume signal occurred, and then multiplied by $\alpha$ to generate a corrected volume signal.

Alpha is a correction factor. The electrical field generated by the conductance catheter is known to be inhomogenous and as a result the raw conductance signal underestimates stroke volume. The raw conductance signal is therefore multiplied by alpha, defined as the ratio of flow probe conductance stroke volume to raw conductance stroke volume.

Steady state parallel conductance ($G_p$) is determined via the hypertonic saline technique described by Baan et al. (Baan J, Van Der Velde E T, De Bruin H G, Smeenk G J, Van Dijk A D, Temmerman D, Senden J, Buis B. Continuous measurement of left ventricular volume in animals and humans by conductance catheter. Circulation 70: 812–823, 1984, incorporated by reference herein), which was modified for the mouse. A 20-μL bolus of hypertonic saline (1.5%) was directly injected into the right ventricle with a 30G needle attached to PE 10 tubing. As the saline entered the left ventricle following transit through the lungs it transiently increased blood conductivity. This results in an increase in the left ventricular conductance signal and theoretically no change in left ventricular hemodynamics. Conductance at end-systole ($G_{es}$) and end-diastole ($G_{ed}$) are related during saline wash-in:

$$G_{es} = m \cdot G_{ed} + b \qquad (3)$$

where m is the slope and b is the intercept of the regression line. The intercept between the linear regression of $G_{es}$ and $G_{ed}$ and the line of identity (i.e. $G_{es}=G_{ed}$) is $G_p$. This is based on the assumption that when the conductivity of blood is zero, all current is conducted through surrounding structures. $G_p$ can be solved as follows:

$$G_p = b/(1-m) \qquad (4)$$

Calculation of mouse blood volume from multiple frequency data. The conductance signal output generated from the mouse varies with time and is a combination of signals arising from both the blood and myocardium. Derivation of left ventricular chamber volume requires the assumption that while resistivity of myocardium varies as a definable function of frequency, resistivity of blood is independent of frequency. As such, $$G_{edf1} = G_{m,f1} + G_{b,edf1} \qquad (5)$$

and $$G_{edf2} = G_{m,f2} + G_{b,edf2} \qquad (6)$$

where $G_{ed}$ is total measured conductance at end-diastole, $G_m$ is conductance from muscle, $G_b$ is conductance from left ventricular blood, and $f_1$ and $f_2$ are the test frequencies used empirically. Since $$G_{b,edf1} = G_{b,edf2} \qquad (7)$$

subtraction of equation (5) from (6) yields:

$$G_{edf1} - G_{edf2} = G_{m,f1} - G_{m,f2} \qquad (8)$$

The resistivity of muscle is defined experimentally (FIG. 7), and relates to conductance by an end-diastolic constant ($k_{ed}$) such that $$G_{m,f1} = k_{ed}/\rho_{f1}$$

and $$G_{m,f2} = k_{ed}/\rho_{f2} \qquad (9)$$

By substitution:

$$G_{edf1} - G_{edf2} = k_{ed}(1/\rho_{f1} - 1/\rho_{f2}) \qquad (10)$$

allowing solution for $k_{ed}$. Applying this constant to equation (5) provides a value for $G_{b,edf1}$ in μS. The same approach can be applied to end-systole where a different $k_{ES}$ would be determined since k depends on shape, or any other time throughout the cardiac cycle.

The conversion of conductance to volume for dual frequency was performed as follows. The relationship from the input conductance to the output voltage was determined as described for the single frequency method above. This relationship is added to the standard data acquisition software, and allows to obtain instantaneous conductance ($G_{f1}$ and $G_{f2}$) from the beating mouse heart. Since $\rho_{f1}$ and $\rho_{f2}$ was previously measured in other mice of the same be strain, the shape constant k in equation (10) could be solved. Once k is known, the instantaneous muscle conductance for either frequency according to equation (9) could be solved, substitute muscle conductance into equation (5) or (6), and then solve for blood conductance. Equation (1) is used to convert conductance to volume. Assuming $\alpha=1$, maximal and minimal volume are determined, and the difference (stroke volume). $\alpha$ is then calculated as the ratio of flow probe stroke volume and dual frequency derived stroke volume. Finally, the raw dual frequency volume is multiplied by alpha to derive corrected dual frequency volume.

System Calibration. To demonstrate that the miniaturized mouse conductance catheter would generate a constant conductance output at different frequencies, the following was done. Saline with resistivities of 62, 78, 93, 109, and 125 Ω·cm, which span the reported resistivities of blood (Trautman E D, Newbower R S. A practical analysis of the electrical conductivity of blood. IEEE Trans Biomed Eng 30: 141–153, 1983, incorporated by reference herein), were used. The saline was placed in 6 mm diameter test tubes in an $H_2O$ bath at 37° C. and the conductance catheter was centered in the saline. Voltage output was determined at frequencies ranging from 500 Hz to 100 kHz.

Studies in mice. The protocol was approved by the Institutional Animal Care and Use Committee at the University of Texas Health Science Center at San Antonio and conformed with "Guidelines for the Care and Use of Laboratory Animals" (NIH publication No. 86-23, revised in 1985, incorporated by reference herein) and "Principles of Laboratory Animal Care" (published by the National society for Medical Research, incorporated by reference herein). CD-1 mice (n=19) weighing 20 to 30 g were anesthetized by administering methoxyflurane (Metofane, Pitman-Moore, Inc., Mundelein, Ill.) in a closed chamber, followed by urethane (1000 mg/kg, i.p) and etomidate (25 mg/kg, i.p.). Respiration was controlled through a tracheostomy cannula and the animals were mechanically ventilated with room air at 60 breaths/min using a rodent ventilator (Harvard Apparatus Model 680, South Natick, Mass.). The chest was entered via an anterior thoracotomy. A small animal blood flow meter (T 106, Transonic Systems Inc., Ithaca, N.Y.) was placed around the aorta. The flow meter was placed on the descending thoracic aorta immediately above the level of the diaphragm. For technical reasons, it could not be placed on the ascending thoracic aorta. In 5 additional CD-1 mice examined by echocardiography (Feldman M D, Erikson J M, Mao Y, Freeman G L. Comparison of three techniques to assess mouse ventricular volume. Circulation 100 (No. 18), I-759, 1999, incorporated by reference herein), 72.5±4.8% of the stroke volume ejected into the ascending thoracic aorta was determined to be present in the descending thoracic aorta. Since the flow probe was placed around the descending thoracic aorta, stroke volume flow probe presented in Table 1 was normalized to correct for stroke volume lost to the vessels of the aortic arch.

Figure 7:
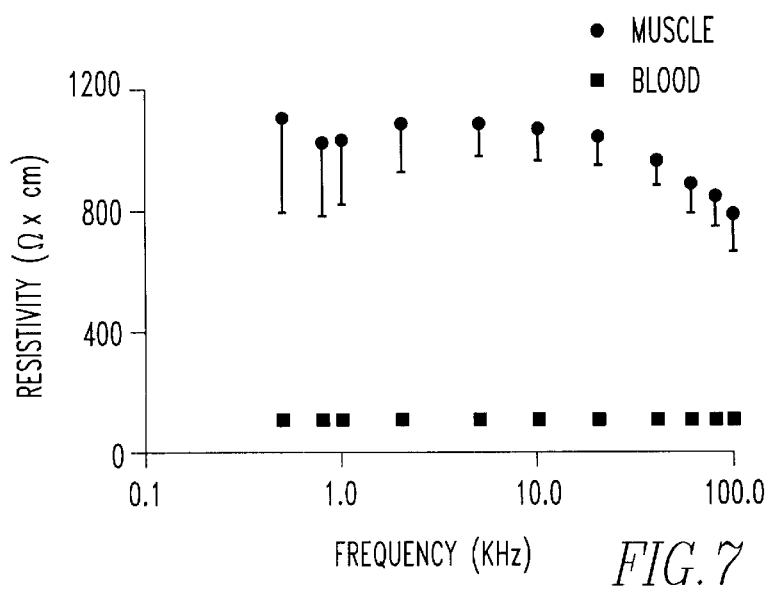
FIG. 7 is a plot of the resistivity versus frequency of mouse blood determined by placing the miniaturized mouse conductance catheter in a tube containing blood, and of mouse left ventricular myocardium derived from the epicardial suction tetrapolar electrodes. Mean and standard deviation from 8 mice are shown. The resistivity of mouse blood is constant despite frequencies ranging from 500 Hz to 100 kHz $^{(R)}$=0.183, p=0.015). In contrast, the myocardial resistivity falls as frequency increases over the same frequency range $^{(R)}$=−0.441, p=0.001).

An apical stab was made in the heart with a 30G needle, and the miniaturized mouse conductance catheter was advanced retrograde into the left ventricle along the cardiac long axis with the proximal electrode just within the myocardial wall of the left ventricular apex (FIG. 7). The Millar Conductance System (MCS-100, Millar Instruments Inc., Houston, Tex.) was used as the signal processor, and individual frequencies were generated sequentially with a Signametrics Complex DDS Generator (SM-1030, Seattle, Wash.) in 8 mice. The voltage outputs were acquired at a sampling rate of 1000 Hz and stored on disc. They were converted to conductance and then to volume as described above. In addition, a signal processor was used with which two frequencies (10 and 100 kHz) were generated simultaneously from the Signametrics Complex DDS Generator (SM-1030, Seattle, Wash.).

Determination of mouse muscle and blood resistivity. To determine the conductance of in vivo myocardium, a customized suction tetrapolar electrode device was developed using silver-coated copper wire. The 4 electrodes ended as blunt probes separated by 0.25 mm that were contained within a 1 mm plastic tube which could be attached to a vacuum, similar to the device developed for the canine by Steendijk et al (Steendijk P, Mur G. Van Der Velde E, Baan J. The four-electrode resistivity technique in anisotropic media: theoretical analysis and application on myocardial tissue in vivo. IEEE Trans Bio Med Eng 40: 1138–1148, 1993, incorporated by reference herein). This enabled the device to be applied directly to the epicardium of the beating mouse myocardium to determine frequency—resistivity relationships at the same time the miniaturized mouse conductance catheter was inserted into the left ventricle to determine frequency-conductance relationships (n=8).

To demonstrate that the resistivity of mouse blood was constant at different frequencies, six additional CD-1 mice were n bled. The blood from each animal was placed in 6 mm diameter test tubes in a $H_2O$ bath at 37° C. and the conductance catheter was centered in the blood. Resistivity was determined at frequencies ranging from 500 Hz to 100 kHz.

Evidence that the electric field is extending into the mouse myocardium. To demonstrate the limitations of the hypertonic saline technique and the importance of an alternative technique such as multiple frequency measurement, the load dependence of $G_p$ was demonstrated. Six additional CD-1 mice underwent the in vivo protocol outlined above. Following the acquisition of baseline conductance and flow probe data at 10 kHz, sustained aortic occlusion was performed by placing tension on a suture around the descending thoracic aorta until a new steady state systolic pressure was achieved with increased intra-ventricular pressure. Hypertonic saline determination of $G_p$ was performed at baseline and at increased load.

Mouse heart morphologic measurements: To determine the wall thickness to chamber ratio (Ganau A, Devereux R B, Roman M J, De Simone G, Pickering T G, Sergio P, Vargiu P, Simongini I, Laragh J H. Patterns of left ventricular hypertrophy and geometric remodeling in essential hypertension. J Am Coll Cardiol 19: 1550–1558, 1992; Reichek N, Devereux R B. Reliable estimation of peak left ventricular systolic pressure by M-mode echographic-determined end-diastolic relative wall thickness: identification of severe valvular aortic stenosis in adult patients. Am Heart J 103; 202–209, 1982, both of which are incorporated by reference herein), 3 mouse hearts were cut longitudinally in 4 micron sections with a microtome and mounted on microscope slides. Staining was performed with hematoxylin and eosin. Measurements of anterior and posterior wall thickness, and chamber diameter were made at the mid-papillary muscle level with planimetry.

Calculations: Conductance derived pressure—volume data was analyzed with software developed by us (PVAN) and modified by Millar Instruments, Houston, Tx. Heart rate was determined as 1/R-R interval, end-systolic pressure was pressure at the point of maximal P/V ratio, end-diastolic pressure was the pressure at the R wave, end-systolic volume (ESV) was the minimal left ventricular volume, end-diastolic volume (EDV) was the maximal left ventricular volume, and stroke volume the difference (EDV−ESV).

Statistics: Within each mouse, relationships between frequency (logarithmic scale) and resistivity and between frequency and conductance were examined by scatter plots and by computing Spearman's non-parametric rank correlation coefficients. Non-parametric analyses were used because most relationships were monotone but not necessarily linear. Cochran-Mantel-Haenszel statistics based on ranks were computed to obtain global measures of correlation controlling for individual mouse effects. The average Spearman's correlation coefficients, averaged over all pairs of mice, were then computed from the resulting Friedman's test statistics (Conover W J. *Practical Nonparametric Statistics.* John Wiley and Sons, Inc., New York, 1971. pp 271–272, incorporated by reference herein). All computations were performed using SAS (Version 6.11, SAS Institute, Cary, N.C.).

Figure 5A:
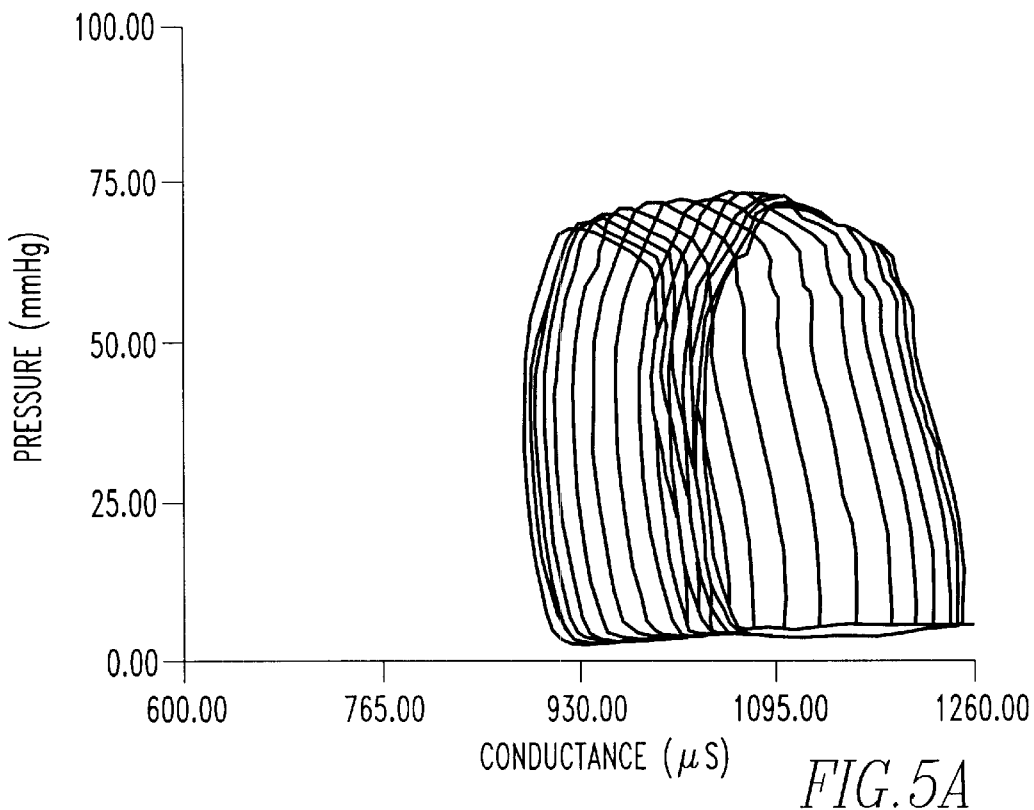
FIGS. 5a and 5b refer to data from an individual mouse during calculation of single frequency steady state parallel conductance (Gp) with bolus injection of hypertonic saline.
Figure 5B:
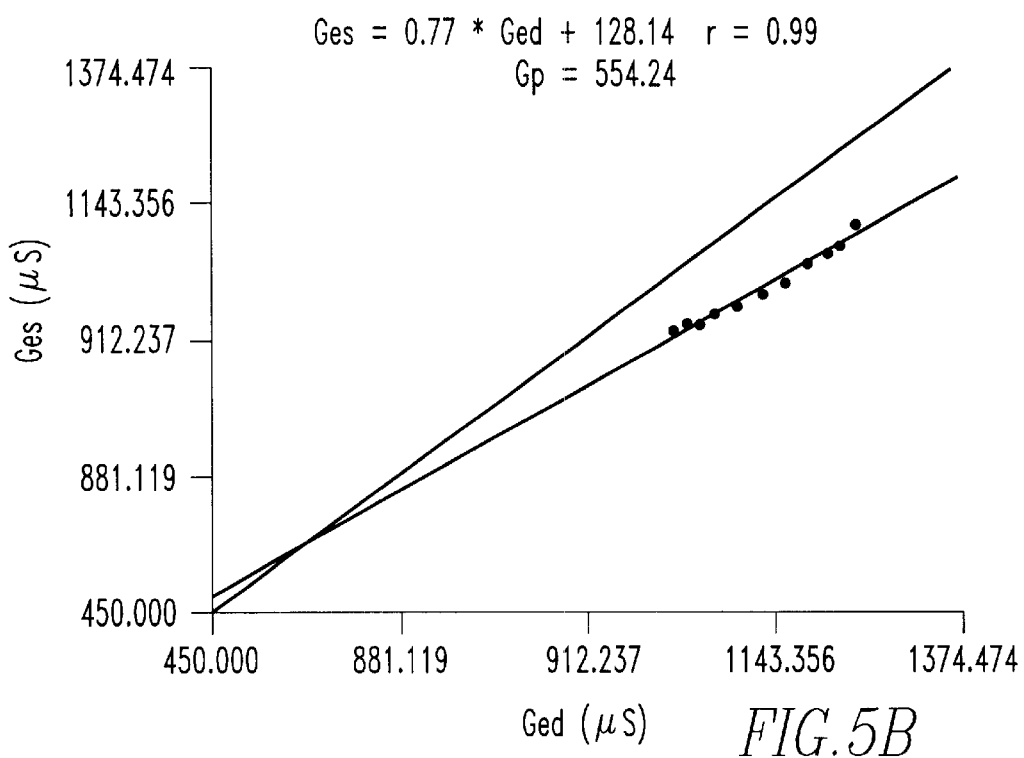

FIGS. 5a and 5b show an example of data from an individual mouse during calculation of single frequency steady state parallel conductance ($G_p$) with bolus injection of hypertonic saline. FIG. 5a is the conductance derived left ventricular pressure-conductance relationships during hypertonic saline wash-in used to calculate end-systolic and end-diastolic conductance on a beat-by-beat basis shown in FIG. 5b. There are beat-by-beat changes in end-diastolic conductance greater than end-systolic conductance. FIG. 5b demonstrates the calculation of parallel conductance using equations (3) and (4) in the Methods. Parallel conductance was 554.24 µS.

Figure 6:
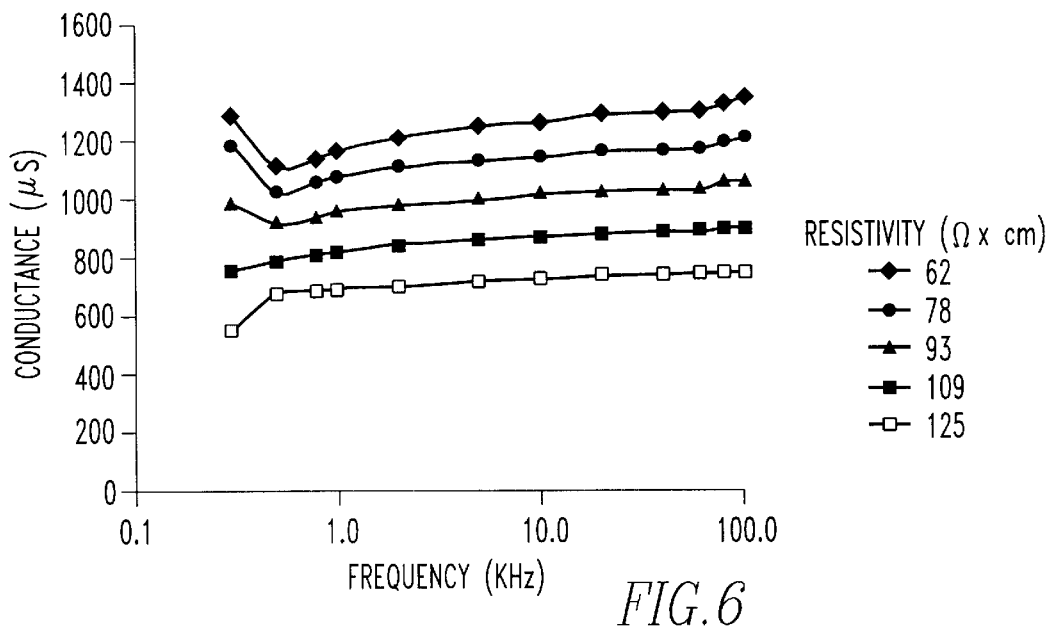
FIG. 6 shows the data of Frequency (kHz) versus Conductance output (µS) of the signal generator/processor is shown. This demonstrates that the conductance and therefore current output of the signal generator/processor is constant over the frequencies examined. This is critical since voltage is converted to conductance, and a varying source current would confound interpretation (since G=I/V, where G=conductance, V=voltage, and I=current, then I must be constant over the frequencies examined for voltage to be converted to conductance). Moreover, the constant current output persisted despite a doubling of resistivity of saline from 62 to 125 Ω·cm.

FIG. 6 shows the regression lines of frequency (kHz) versus conductance (µS) of the signal processor (MCS, Houston, Tex.). These studies demonstrate that the conductance output of the signal processor is constant over the frequencies examined. This is critical since voltage is converted to conductance, and a varying source current would confound interpretation (since G=I/V, where G=conductance, V=voltage, and I=current, then I must be constant over the frequencies examined for voltage to be converted to conductance). Moreover, the constant current output persisted despite a doubling of resistivity of saline from 62 to 125 Ω·cm.

FIG. 7 is a plot of the resistivity versus frequency of mouse blood determined by placing the miniaturized mouse conductance catheter in a tube containing blood, and of mouse left ventricular myocardium derived from the epicardial suction tetrapolar electrodes. The mean and standard deviation from 8 mice are shown. The resistivity of mouse blood is constant despite frequencies ranging from 500 Hz to 100 kHz ®=0.183, p=0.015). In contrast, the myocardial resistivity falls as frequency increases over the same frequency range ®=−0.441, p=0.001).

Figure 8:
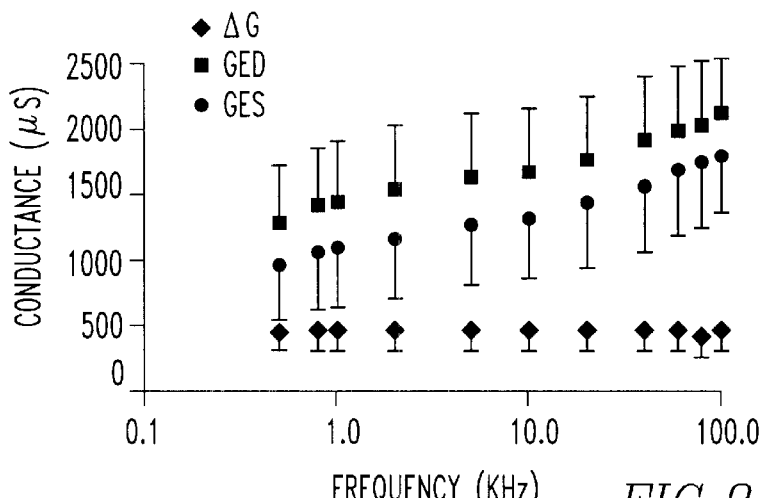
FIG. 8 is a plot of conductance as a function of frequency, measured in vivo by the conductance catheter placed in the same 8 mice shown in FIG. 4. The conductance was not corrected for parallel conductance (Gp) or electrical field in-homogeneity (α). As frequency increases, both end-diastolic conductance $^{(R)}$=0.987, p=0.001) and end-systolic conductance $^{(R)}$=0.985, p=0.001) increase. In contrast, as frequency increases there is a decrease in the difference between end-diastolic and systolic conductance (ΔG, r=−0.200, p=0.008) although the correlation coefficient is low.

FIG. 8 is a plot of measured conductance, as a function of frequency, measured in vivo by the conductance catheter placed in the same 8 mice shown in FIG. 7. The conductance is not corrected for parallel conductance ($G_p$) or electrical field inhomogeneity (α). As frequency increases, both end-diastolic conductance ®=0.987, p=0.001) and end-systolic conductance ®=0.985, p=0.001) increase. In contrast, as frequency increases there is a decrease in the difference between end-diastolic and end-systolic conductance (ΔG, r=−0.200, p=0.008) although the correlation coefficient is low.

Figure 9:
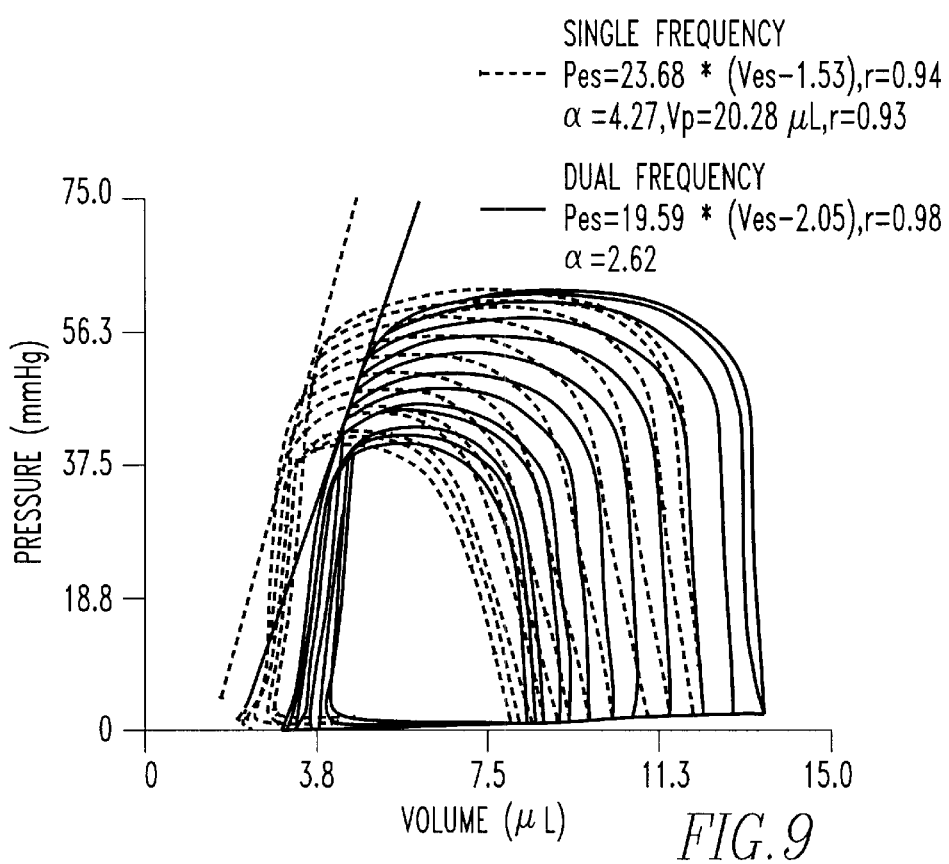
FIG. 9 is a plot of left ventricular pressure-volume relationships during the identical caval occlusion is shown for data derived from the simultaneous dual-frequency method (10 and 100 kHz, solid lines) and single-frequency method (10 kHz, dotted lines) corrected with the saline technique. As is usually evident, the 2 methods gave different end-systolic elastance ($V_0$=1.53 or 2.05 µl) and volumes ($V_{es}$). The left ventricular weight of this mouse was 115 mg, compared with 133±8 mg for the mouse data displayed in Table 1, which may explain the smaller volumes shown here. $P_{es}$, end-systolic pressure; $V_p$, parallel conductance.

Table 1 is a comparison of the end-diastolic volume, end-systolic volume, and stroke volumes calculated by the two methods. The first method uses multiple frequencies as proposed in this manuscript, according to equation (5) through (10). The second method uses that proposed by Baan and coworkers (Baan J, Van Der Velde E T, De Bruin H G, Smeenk G J, Van Dijk A D, Temmerman D, Senden J, Buis B. Continuous measurement of left ventricular volume in animals and humans by conductance catheter. Circulation 70: 812–823, 1984, incorporated by reference herein), where the raw conductance signal is corrected for parallel conductance ($G_p$) and electrical field inhomogeneity ($\alpha$). For this analysis, two frequencies were used (10 and 100 kHz), and these frequencies were delivered simultaneously. These frequencies correspond to maximal differences in myocardial resistivity (FIG. 7), and a flat current output of the signal processor (FIG. 9).

The baseline hemodynamics of these 6 mice included an end-systolic pressure of 57±6 mm Hg, heart rate of 439±19 bpm, and flow probe stroke volume of 16.19±3.29 $\mu$L/beat. The use of two simultaneous frequencies (10 and 100 kHz) to calculate volumes per the new method proposed in this manuscript yielded a raw stroke volume of 6.0±1.3 $\mu$L/beat (not corrected by $G_p$ or $\alpha$), end-diastolic volume of 40±8 $\mu$L, and end-systolic volume of 24±7 $\mu$L. Alpha was 2.75. The shape constants $k_{ed}$ and $k_{es}$ were 6.1±0.6 and 5.3±0.4 mm, respectively, (p<0.001). The standard method (single frequency—saline) yielded a raw stroke volume of 4.3±0.8 $\mu$L/beat (not corrected by $G_p$ or $\alpha$), end-diastolic volume of 23±4 $\mu$L, and end-systolic volume of 8±2 $\mu$L. Alpha was 3.63±1.04. As the multi-frequency derived stroke volume, end-systolic volume, and end-diastolic volume increased, so did the same parameters derived with the standard method of calculation (SV r=0.916, ESV r=0.713, and EDV r=0.933). The raw dual frequency stroke volume was larger than the raw single frequency stroke volume (p<0.001, not corrected by $G_p$ or $\alpha$).

To demonstrate the importance of simultaneous input of two frequencies, an additional 8 mice had the same hemodynamic parameters determined, but the different frequencies were used sequentially. The baseline hemodynamics of these mice included an end-systolic pressure of 65±13 mm Hg, heart rate of 446±56 bpm, and flow probe stroke volume of 15±4 $\mu$L/beat. The use of two frequencies (10 and 100 kHz or 10 and 60 kHz) to calculate volumes per the new method proposed in this manuscript yielded a stroke volume of 6±2 $\mu$L/beat, end-diastolic volume of 21±9 $\mu$L, and end-systolic volume of 12±7 $\mu$L. The standard method yielded a stroke volume of 10±4 $\mu$L/beat, end-diastolic volume of 27±12 $\mu$L, and end-systolic volume of 13±10 $\mu$L. As the multi-frequency derived stroke volume, end-systolic volume, and end-diastolic volume increased, so did the same parameters derived with the standard method of calculation (SV r=0.854, ESV r=0.686, and EDV r=0.874).

Table 2 is a comparison of $G_p$ at steady state conditions and when afterload was increased by sustained aortic occlusion. Studies were performed on 6 additional mice at a single frequency (10 kHz). The baseline $G_p$ of 14.6±7.0 increased to 19.2±7.9 $\mu$L with sustained afterload (p<0.01). The heart rate did not change (446±74 to 439±43 bpm, p=NS), but end-systolic pressure (52±8 to 80±11 mm Hg, p<0.01) and end-diastolic pressure both increased (3±1 to 4±2 mm Hg, p<0.01).

At lower frequencies, the field is confined to the left ventricular cavity and to a lesser degree the myocardium. Likewise, at higher frequencies the electric field generated is not confined to the left ventricular cavity but extends into the myocardium. The basis for this proposal, which was confirmed in the in vivo mouse heart, is that myocardial resistivity decreases with increasing frequency (Epstein B R, Foster K R. Anisotropy in the dielectric properties of skeletal muscle. Med Biol Eng Comput 21: 51–55, 1983; Schwan H P, Kay C F. Specific resistance of body tissues. Circ Res IV: 664–670, 1956; Steendijk P, Mur G, Van Der Velde E, Baan J. The four-electrode resistivity technique in anisotropic media: theoretical analysis and application on myocardial tissue in vivo. IEEE Trans Bio Med Eng 40: 1138–1148, 1993; Steendijk P, Mur G, Van Der Velde E, Baan J. Dependence of anisotropic myocardium electrical resistivity on cardiac phase and excitation frequency. Basic Res Cardiol 89: 411–426, 1994; Zheng E, Shao S, Webster J G. Impedance of skeletal muscle from 1 Hz to 1 MHz. IEEE Trans Biomed Eng 31: 477–483, 1984, all of which are incorporated by reference herein), while blood resistivity is constant at different frequencies (Schwan H P. Electrical properties of blood and its constituents: alternating current spectroscopy. Blut 46: 185–197, 1983, incorporated by reference herein). At higher excitation frequency greater end-diastolic and end-systolic conductance and smaller $\Delta G$ is generated. Left ventricular blood volume using 2 frequencies simultaneously was determined. Measured resistivity of mouse myocardium was combined with an analytical approach, and was able to extract an estimate of left ventricular blood volume from the raw conductance signal.

One advantage of dual frequency conductance documented is was the detection of a larger amount of stroke volume. The flow probe measured 16.19±3.29 compared to 4.3±0.8 $\mu$l/beat for the single field conductance technique. The dual field technology detected 6.0±1.3 $\mu$l/beat. As a result, the correction factor for electrical field inhomogenity ($\alpha$) as the ratio of flow probe stroke volume to raw conductance stroke volume would be smaller with dual frequency. Since the final step in converting the instantaneous voltage output generated by the conductance catheter to volume is multiplication by $\alpha$, there would be less magnification of any error. A second advantage is that dual field eliminates the need to administer hypertonic saline to determine steady state parallel conductance. The conductance technique and equation (1) require knowledge of the resistivity of blood which is always changing in a given mouse as more hypertonic saline is injected. Given the very small blood volume of mice it is not practical to measure this changing resistivity for every condition during each experiment.

The mean ejection fraction (EF) for the dual frequency method calculated for the six mice presented in Table 1 is 42±7%. The mean ejection fraction for these same mice calculated with the single frequency method is 68±9%. Given the open chest preparation, the heart rate and the instrumentation used in the present study, 42% is likely a more realistic value. Why does single frequency conductance overestimate EF in the mouse? The stroke volume determined by the dual and single frequency methods will be equal since both are corrected by the flow probe stroke volume. The single frequency end-diastolic volume is smaller than dual frequency end-diastolic volume. Therefore the calculated EF will always be larger with the single frequency method.

The smaller end-diastolic volume determined with single frequency compared to dual frequency is due to overestimation of parallel conductance ($G_p$). The hypertonic saline method as originally described by Baan assumes no significant effect on left ventricular volume or performance (Baan J, Van Der Velde E T, De Bruin H G, Smeenk G J, Van Dijk A D, Temmerman D, Senden J, Buis B. Continuous measurement of left ventricular volume in animals and humans by conductance catheter. Circulation 70: 812–823, 1984, incorporated by reference herein). That has been confirmed in larger animals where approximately 2% of the left ventricular blood volume is injected. In the mouse, the injection of 20 µl of hypertonic saline in the right ventricle represents a large portion of left ventricular blood volume. This causes significant beat-by-beat changes in end-diastolic greater than end-systolic conductance as demonstrated in FIG. 5a. This is anticipated since the bolus of hypertonic saline produces a sudden increase in preload without a change in contractility. To determine parallel conductance $G_{es}$ is plotted on the ordinate, and $G_{ed}$ on the abscissa as shown in FIG. 5b, and $G_p$ is determined as the intercept of the extrapolated data with the line of identity. Since $G_{ed}$ is changing faster than $G_{es}$, violating the assumptions of Baan (Baan J, Van Der Velde E T, De Bruin H G, Smeenk G J, Van Dijk A D, Temmerman D, Senden J, Buis B. Continuous measurement of left ventricular volume in animals and humans by conductance catheter. Circulation 70: 812–823, 1984, incorporated by reference herein), then the intersection with the line of identity will be artificially increased. The result will be an overestimation of $G_p$, a smaller end-diastolic volume, and an overestimated EF with the single frequency technique.

The derivation of left ventricular blood volume from multiple frequency data requires two assumptions. The first is that mouse myocardial resistivity determined in vivo on the epicardial surface by the suction tetrapolar electrode is similar to the myocardial resistivity component of the miniaturized mouse conductance signal generated from within the left ventricular chamber. The traditional method to determine myocardial resistivity is to place in vitro epicardial pins or electrode holders onto the myocardium (Epstein B R, Foster K R. Anisotropy in the dielectric properties of skeletal muscle. Med Biol Eng Comput 21: 51–55, 1983; Lofgren B. The electrical impedance of a complex tissue and its relation to changes in volume and fluid distribution. Acta Physiologica Scandinavia 23: 3–51, 1951; Rush S, Abildskov J A, McPee R. Resistivity of body tissues at low frequencies. Circ Res XII: 40–50, 1963; Weidman S. Electrical constants of trabecular muscle form mammalian heart. J Physiol 210: 1041–1054, 1970, all of which are incorporated by reference herein). This method is limited by injury from the electrodes, and ischemia to the myocardium as an in vitro preparation. Ischemia has previously been shown to significantly increase myocardial resistivity (Fallert M A, Mirotznik M S, Downing S W, Savage E B, Foster K R, Josephson M E, Bogen D K. Myocardial electrical impedance mapping of ischemic sheep hearts and healing aneurysms. Circulation 87: 199–207, 1993; Van Oosterom A, De Boer R W, Van Dam R T. Intramural resistivity of cardiac tissue. Med and Biol Eng and Comput 17: 337–343, 1979, both of which are incorporated by reference herein). The blunt suction tetrapolar electrodes used in the current study solves both of these problems, and is similar in concept to that employed by Baan and coworkers (Steendijk P, Mur G, Van Der Velde E, Baan J. The four-electrode resistivity technique in anisotropic media: theoretical analysis and application on myocardial tissue in vivo. IEEE Trans Bio Med Eng 40: 1138–1148, 1993, incorporated by reference herein).

The second assumption is that mouse myocardial resistivity varies with frequency, while mouse blood resistivity does not vary with excitation frequency. The observation that muscle resistivity decreases as the frequency of the input signal increases was established in the 19$^{th}$ century (Hermann L. Ueber eine wirkung galvanischer strome auf muskeln und nervern. Pflugers Arch Ges Physiol 5: 223–275, 1871, incorporated by reference herein) and has been reconfirmed by several groups (Epstein B R, Foster K R. Anisotropy in the dielectric properties of skeletal muscle. Med Biol Eng Comput 21: 51–55, 1983; Schwan H P, Kay C F. Specific resistance of body tissues. Circ Res IV: 664–670, 1956; Steendijk P, Mur G, Van Der Velde E, Baan J. The four-electrode resistivity technique in anisotropic media: theoretical analysis and application on myocardial tissue in vivo. IEEE Trans Bio Med Eng 40: 1138–1148, 1993; Steendijk P, Mur G, Van Der Velde E, Baan J. Dependence of anisotropic myocardium electrical resistivity on cardiac phase and excitation frequency. Basic Res Cardiol 89: 411–426, 1994; Zheng E, Shao S. Webster J G. Impedance of skeletal muscle from 1 Hz to 1 MHz. IEEE Trans Biomed Eng 31: 477–483, 1984, all of which are incorporated by reference herein). This construct holds that at high frequency, the cell membranes should be effectively short-circuited, with tissue conductance equal to the conductivity of cytoplasm. As a result, resistivity falls. In contrast, at low frequency, the field also travels through the cell membrane that has higher resistivity. The tetrapolar suction electrodes with electrode spacing of 0.25 mm to be significantly less than the 1.2±0.1 mm (n=3) average anterior myocardium thickness determined morphologically. A ratio of myocardial thickness to electrode separation of greater than 1 insures that the electrical field is confined to the myocardium, and does not extend into the left ventricular blood (Steendijk P, Mur G, Van Der Velde E, Baan J. The four-electrode resistivity technique in anisotropic media: theoretical analysis and application on myocardial tissue in vivo. IEEE Trans Bio Med Eng 40: 1138–1148, 1993, incorporated by reference herein). Moreover, since the intramyocardial conductance signal will pass through a substantial depth of myocardium, the fiber orientation through which it passes will vary. Since myocardial blood volume varies with the phase of the cardiac cycle, and resistivity of cardiac muscle differs with fiber direction (Epstein B R, Foster K R. Anisotropy in the dielectric properties of skeletal muscle. Med Biol Eng Comput 21: 51–55, 1983; Rush S, Abildskov J A, McFee R. Resistivity of body tissues at low frequencies. Circ Res XII: 40–50, 1963; Steendijk P, Mur G, Van Der Velde E, Baan J. The four-electrode resistivity technique in anisotropic media: theoretical analysis and application on myocardial tissue in vivo. IEEE Trans Bio Med Eng 40: 1138–1148, 1993; Steendijk P, Mur G, Van Der Velde E, Baan J. Dependence of anisotropic myocardium electrical resistivity on cardiac phase and excitation frequency. Basic Res Cardiol 89: 411–426, 1994, all of which are incorporated by reference herein), these could all be sources of variation in determining in vivo myocardial resistivity.

Therefore, a lumped value for resistivity, independent of fiber orientation or phase of the cardiac cycle was chosen.

There has been a previous study attempting to estimate left ventricular offset volume using two stimulation frequencies. Gawne and coworkers (Gawne T J, Kristen S G, Goldstein R E. Estimating left ventricular offset volume using dual-frequency conductance catheters. J Appl Physiol 63: 872–876, 1987, incorporated by reference herein) also took advantage of the fact that myocardial resistivity is dependent on input frequency while blood resistivity is independent of input frequency. They hypothesized that stroke volume would be independent of input frequency while minimal volume (end-systolic volume) would vary with input frequency. Therefore, the change in end-systolic volume with frequency would be due to quantifiable parallel conductance. However, their approach could only be applied during steady-state conditions and therefore could not be applied with changing loading conditions to generate end-systolic elastance. Furthermore, as shown in FIG. 7, apparent stroke volume should not be constant but fall at increasing frequency due to a less dense electric field in the left ventricular chamber. Apparent stroke volume fell with increasing input frequency while Gawne (Gawne T J, Kristen S G, Goldstein R E. Estimating left ventricular offset volume using dual-frequency conductance catheters. J Appl Physiol 63: 872–876, 1987, incorporated by reference herein) did not. See this. The frequencies examined by Gawne (Gawne T J, Kristen S G, Goldstein R E. Estimating left ventricular offset volume using dual-frequency conductance catheters. J Appl Physiol 63: 872–876, 1987, incorporated by reference herein) did not exceed 33 kHz, a frequency maximum in the mouse that did not change myocardial resistivity. Finally, Gawne felt that an analytic solution to this problem of using multiple frequency signals to solve for instantaneous parallel conductance was not possible due to the complex, changing geometry of the heart. This problem was solved with the introduction of a shape constant, k. By determining the instantaneously changing shape constant during the cardiac cycle and during changing loading conditions, a more robust approach is had that can now be applied not just during steady state but also during the generation of load-independent measures of contractility.

The use of dual frequency conductance is relevant to crossing the major hurdle of applying conductance measurements to evaluate left ventricular function in the pressure-volume plane. A traditional limitation of conductance measurements has been changing parallel conductance during occlusion of the inferior vena cava to generate end-systolic elastance, effective arterial elastance, and additional measures of ventricular function generated from pressure-volume analysis (Boltwood C M, Appleyard R F, Glantz S A. Left ventricular volume measurement by conductance catheter in intact dogs: parallel conductance volume depends on left ventricular size. Circulation 80: 1360–1377, 1989; Cassidy S C, Teitel D F. The conductance catheter technique for measurement of left ventricular volume in young piglets. Pediatr Res 31: 85–90, 1992, both of which are incorporated by reference herein). The currently accepted technique of using small injections of hypertonic saline to correct for parallel conductance is only accurate during steady state conditions (Baan J, Van Der Velde E T, De Bruin H G, Smeenk G J, Van Dijk A D, Temmerman D, Senden J, Buis B. Continuous measurement of left ventricular volume in animals and humans by conductance catheter. Circulation 70: 812–823, 1984; Lankford E B, Kass D A, Maughan W L, Shoukas A A. Does parallel conductance vary during a cardiac cycle? Am J Physiol 258 (Heart Circ Physiol 27): H1933–H1942, 1990, both of which are incorporated by reference herein). Small and physically insignificant changes in parallel conductance occur throughout the cardiac cycle (Lankford E B, Kass D A, Maughan W L, Shoukas A A. Does parallel conductance vary during a cardiac cycle? Am J Physiol 258 (Heart Circ Physiol 27): H1933–H1942, 1990; Szwarc R S, Laurent D, Allegrini P R, Ball H A. Conductance catheter measurement of left ventricular volume: evidence for non-linearity within cardiac cycle. Am J Physiol 268 (Heart Circ Physiol 37): H1490–H1498, 1995; White P A, Chaturvedi R R, Shore D, Lincoln C, Szwarc R S, Bishop A J, Oldershaw P J, Redington A N. Left ventricular parallel conductance during cardiac cycle in children with congenital heart disease. Am J Physiol 273 (Heart Circ Physiol 42): H295–H302, 1997, all of which are incorporated by reference herein). However, during a change in loading conditions, parallel conductance is also changing (Boltwood C M, Appleyard R F, Glantz S A. Left ventricular volume measurement by conductance catheter in intact dogs: parallel conductance volume depends on left ventricular size. Circulation 80: 1360–1377, 1989; Cassidy S C, Teitel D F. The conductance catheter technique for measurement of left ventricular volume in young piglets. Pediatr Res 31: 85–90, 1992, both of which are incorporated by reference herein). This was confirmed in the current study where sustained aortic occlusion which allowed a significant increase in aortic pressure increased $G_p$ from 14.6±7.0 to 19.2±7.9 $\mu$L (p<0.01, Table 2) in six mice. Occlusion of the inferior vena cava results in the left ventricle shrinking around a fixed electric field generated from a conductance catheter. Therefore, the amount of field leakage into the left ventricular myocardium and surrounding structures changes instantaneously.

In conclusion, left ventricular blood volume in the mouse with a miniaturized multi-frequency mouse conductance system could be estimated. Such an approach has the capability to determine instantaneous parallel conductance and determine an accurate estimate of ventricular function with left ventricular pressure-volume analysis, which has not been previously possible.

TABLE 1

Comparison of volumes derived by two methods

| | Hemo-dynamics | Multi Frequency Flow probe | | | | | | Hypertonic saline | | | | | |
|---|---|---|---|---|---|---|---|---|---|---|---|---|---|
| | $P_{es}$ | HR | SV | SV raw | Alpha | $K_{ED}$ | $K_{ES}$ | EDV | ESV | SV raw | Alpha | Gp | EDV | ESV |
| Mouse 1 | 56 | 455 | 15.34 | 4.9 | 3.13 | 6.3 | 5.5 | 45 | 30 | 3.6 | 4.26 | 19.4 | 27 | 12 |
| 2 | 53 | 419 | 22.50 | 6.4 | 3.55 | 5.9 | 5.1 | 50 | 27 | 4.8 | 4.71 | 18.3 | 30 | 7 |
| 3 | 65 | 425 | 15.76 | 8.1 | 1.93 | 7.2 | 6.0 | 31 | 15 | 5.5 | 2.32 | 19.4 | 21 | 8 |
| 4 | 60 | 454 | 18.25 | 6.3 | 2.92 | 5.8 | 5.1 | 48 | 30 | 4.9 | 3.71 | 20.1 | 26 | 7 |
| 5 | 60 | 448 | 15.54 | 5.0 | 3.24 | 5.6 | 5.1 | 45 | 30 | 3.7 | 3.94 | 17.4 | 29 | 11 |
| 6 | 44 | 433 | 9.77 | 5.6 | 1.75 | 6.2 | 5.1 | 21 | 11 | 3.5 | 2.82 | 19.2 | 13 | 3 |
| Mean | 57 | 439 | 16.19 | 6.0* | 2.75 | 6.1** | 5.3 | 40 | 24 | 4.3 | 3.63 | 19.0 | 23 | 8 |
| Std | 6 | 19 | 3.29 | 1.3 | 0.69 | 0.6 | 0.4 | 8 | 7 | 0.8 | 1.04 | 0.7 | 4 | 2 |

$P_{es}$ is end-systolic pressure (mm Hg), HR is heart rate (bpm), SV raw is conductance stroke volume which has not been corrected for Gpi or Alpha ($\mu$L/beat), Alpha is the ratio of Flow probe SV to conductance SV, $K_{ED}$ is the maximum value of the instantaneous shape constant (mm), $K_{ES}$ is the minimum value of the instantaneous shape constant (mm), EDV is left ventricular end-diastolic volume ($\mu$L),
ESV is left ventricular end-systolic volume ($\mu$L), Gp is steady state parallel conductance ($\mu$L). *p < 0.001 Multifrequency SV raw versus Hypertonic saline SV raw. **p < 0.001 $K_{ED}$ versus $K_{ES}$.

TABLE 2

Effect of afterload on parallel conductance

| Mouse | Baseline Gp | Afterload | Baseline HR | Afterload | Baseline $P_{es}$ | Afterload | Baseline $P_{ed}$ | Afterload |
|---|---|---|---|---|---|---|---|---|
| 9 | 7.8 | 12.1 | 502 | 476 | 46 | 75 | 2 | 3 |
| 10 | 16.1 | 26.7 | 511 | 455 | 50 | 74 | 4 | 5 |
| 11 | 19.4 | 23.7 | 352 | 395 | 57 | 76 | 4 | 6 |
| 12 | 25.3 | 28.4 | 512 | 496 | 51 | 79 | 3 | 4 |
| 13 | 8.0 | 11.5 | 431 | 418 | 67 | 103 | 4 | 5 |
| 14 | 11.0 | 12.6 | 367 | 395 | 44 | 75 | 1 | 1 |
| Mean | 14.6 | 19.2* | 446 | 439 | 52 | 80* | 3 | 4* |
| Std | 7.0 | 7.9 | 74 | 43 | 8 | 11 | 1 | 2 |

Afterload is following application of a sustained occlusion of the thoracic aorta, Gp is parallel conductance (μL), HR is heart rate (bpm), $P_{es}$ is end-systolic pressure (mm Hg), $P_{ed}$ is end-diastolic pressure (mmHg).
*p < 0.01 baseline compared to afterload.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for determining cardiac performance in a patient comprising:
    a multifrequency conductance catheter for measuring instantaneous volume of a heart chamber with multifrequencies;
    a mechanism for measuring instantaneous pressure of the heart chamber;
    a mechanism for separating the multifrequencies; and
    a mechanism for signal processing the instantaneous volume and the pressure of the heart chamber to identify mechanical strength of the chamber and for automatically producing a plurality of desired waveforms at desired frequencies for the conductance catheter, said processing mechanism connected to the pressure measuring mechanism, the separating mechanism and the volume measuring mechanism.

2. An apparatus as described in claim 1 wherein the conductance catheter includes a plurality of electrodes to measure at least one segmental volume of the heart chamber.

3. An apparatus as described in claim 2 wherein the plurality of electrodes includes intermediate electrodes to measure an instantaneous voltage signal from the heart, and outer electrodes to which a current is applied from the processing mechanism.

4. An apparatus as described in claim 3 wherein the conductance catheter includes at least one pressure sensor to measure ventricular pressure in the chamber.

5. An apparatus as described in claim 3 wherein the pressure sensor is disposed between the intermediate electrodes and the outer electrodes.

6. An apparatus as described in claim 5 wherein the signal processing mechanism includes a computer with a signal synthesizer and a data acquisition mechanism connected to the catheter.

7. An apparatus as described in claim 6 wherein the signal processing mechanism includes a mechanism for converting conductance into a volume, said converting mechanism connected to the catheter and the computer.

8. An apparatus as described in claim 7 wherein the signal processing mechanism includes a mechanism for producing a drive signal to drive the conductance catheter, said producing mechanism connected to the catheter and the computer.

9. An apparatus as described in claim 8 wherein the converting mechanism includes signal processing circuitry for converting measured conductance to a volume, said signal processing circuitry connected to the catheter and the computer.

10. An apparatus as described in claim 9 wherein the converting mechanism includes a signal conditioning/filter mechanism for reducing noise level of measured conductance, said signal conditioning/filter mechanism connected to the signal processing circuitry and the computer.

11. An apparatus as described in claim 10 wherein the converting mechanism includes a pressure amplifier which amplifies the signal from the solid state pressure sensor, said pressure amplifier connected to the catheter and the signal conditioning/filter mechanism.

12. An apparatus as described in claim 11 wherein the drive mechanism includes an internal oscillator which generates a combined signal source of an amplitude excitation voltage at least at two different frequencies, said internal oscillator connected to the computer and the catheter.

13. An apparatus as described in claim 12 wherein the drive mechanism includes a voltage-to-current amplifier which converts excitation voltage to a current, said voltage-to-current amplifier connected to the internal oscillator and the catheter.

14. An apparatus as described in claim 13 wherein the drive mechanism includes an external input signal synthesizer mechanism for controlling the signal synthesizer of the computer to produce desired waveforms at desired frequencies, said external input signal synthesizer mechanism connected to the computer.

15. An apparatus as described in claim 14 wherein the separating mechanism includes a differential amplifier connected to the intermediate electrodes which extracts a combined signal potential from the intermediate electrodes.

16. An apparatus as described in claim 15 wherein the separating mechanism includes band-pass filters connected to the differential amplifier which separates the frequencies from the combined signal potential.

17. An apparatus as described in claim 16 wherein the signal processing means determines conductance according to $$G_{edf1} - G_{edf2} = k_{ed}(1/\rho_{f1} - 1/\rho_{f2})$$

where $G_{ed}$ is the total measured conductance at end-diastole, $f_1$ and $f_2$ are the test frequencies used, $k_{ed}$ is an end-diastolic constant and ρ is the blood resistancy.

18. An apparatus as described in claim 17 wherein the signal processing means determines conductance according to $$G_{edf1}=G_{m,f1}+G_{b,edf1}$$

and $$G_{edf2}=G_{m,f2}+G_{b,edf2}$$

where $G_m$ is conductance from muscle and $G_b$ is conductance from left ventricular blood.

19. An apparatus as descibed in claim 18 wherein the signal processing means determines conductance according to $$G_{b,edf1}=G_{b,edf2}.$$

20. An apparatus according to claim 19 wherein the signal processing means determines conductance according to $$G_{edf1}-G_{edf2}=G_{m,f1}-G_{m,f2}.$$

21. An apparatus according to claim 20 wherein the signal processing means determines conductance according to $$G_{m,f1}=k_{ed}/\rho_{f1} \text{ and } G_{m,f2}=k_{ed}/\rho_{f2}.$$

22. A method for determining cardiac performance in a patient comprising the steps of:

inserting a conductance catheter into an in viva heart;

sending simultaneously a combined signal consisting of at least two frequencies from a signal source into an amplifier;

applying a current to outer electrodes of the conductance catheter;

measuring an instantaneous voltage signal from the heart with intermediate electrodes of the conductance catheter;

extracting from the intermediate electrodes the combined signal potential from the combined signal;

separating the frequencies from the combined signal potential;

determining the separate conductance associated with each frequency; and identifying pressure volume loops regarding the heart of the patient.

23. A method as described in claim 17 wherein the separating step includes the step of separating with active band-pass filters the frequencies from the combined signal potential.

24. A method as described in claim 18 wherein the extracting step includes the step of extracting from the intermediate electrodes with a common mode rejection differential amplifier the combined signal potential from the combined signal.

25. A method as described in claim 19 wherein the sending step includes the step of sending simultaneously the combined signal consisting of at least two frequencies from a combined signal source into a voltage to current amplifier.

26. A method as described in claim 20 wherein the applying step includes the step of applying a constant current from the voltage to current amplifier to the outer electrodes of the conductance catheter.

27. A method as described in claim 21 wherein the identifying step includes the steps of determining instantaneous pressure of the heart from a pressure sensor of the catheter, determining instantaneous volume of the heart from the conductances associated with each frequency and linking instantaneous pressure and instantaneous volume at the same time over time to generate pressure volume loops regarding the heart of the patient.

* * * * *